United States Patent
Yu et al.

(10) Patent No.: US 12,350,052 B2
(45) Date of Patent: Jul. 8, 2025

(54) MAGNETOCARDIOGRAPHY MEASURING APPARATUS

(71) Applicant: KOREA RESEARCH INSTITUTE OF STANDARDS AND SCIENCE, Daejeon (KR)

(72) Inventors: Kwon-Kyu Yu, Daejeon (KR); Yong-Ho Lee, Daejeon (KR); Jin-Mok Kim, Daejeon (KR); Hyukchan Kwon, Daejeon (KR); Sang Kil Lee, Daejeon (KR); Bo-Kyung Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 230 days.

(21) Appl. No.: 18/307,094

(22) Filed: Apr. 26, 2023

(65) Prior Publication Data

US 2023/0263445 A1      Aug. 24, 2023

Related U.S. Application Data

(63) Continuation of application No. PCT/KR2021/002717, filed on Mar. 5, 2021.

(30) Foreign Application Priority Data

Dec. 7, 2020   (KR) .................. 10-2020-0169438

(51) Int. Cl.
    *A61B 5/243*   (2021.01)
(52) U.S. Cl.
    CPC ...... *A61B 5/243* (2021.01); *A61B 2562/0223* (2013.01); *A61B 2562/046* (2013.01); *A61B 2562/166* (2013.01)

(58) Field of Classification Search
    CPC ............ A61B 5/243; A61B 2562/0223; A61B 2562/046; A61B 2562/166;
    (Continued)

(56) References Cited

U.S. PATENT DOCUMENTS

| 9,823,312 B2 | 11/2017 | Yu et al. |
| 10,426,363 B2 | 10/2019 | Yu et al. |

(Continued)

FOREIGN PATENT DOCUMENTS

| EP | 3267213 A1 | 1/2018 |
| JP | 10-305019 A | 11/1998 |

(Continued)

OTHER PUBLICATIONS

International Search Report, International application No. PCT/KR2021/002717; Sep. 6, 2021; Korean Intellectual Property Office, Daejeon, Republic of Korea.

(Continued)

*Primary Examiner* — Keith M Raymond
*Assistant Examiner* — Andrew W Begeman
(74) *Attorney, Agent, or Firm* — Andrew D. Fortney; Central California IP Group, P.C.

(57) ABSTRACT

A magnetic field measuring apparatus according to an example embodiment includes: an external container; an internal container storing a liquid refrigerant, disposed inside the external container, and including a neck portion having a first diameter and a body portion having a second diameter greater than the first diameter, wherein a space between the internal container and the external container is maintained in a vacuum state; a SQUID sensor module mounting plate disposed below the internal container; a plurality of SQUID sensor modules mounted below the SQUID sensor module mounting plate; and a 4K heat shielding portion formed of a conductive mesh disposed to (Continued)

surround the SQUID sensor module mounting plate and the plurality of SQUID sensor modules.

26 Claims, 14 Drawing Sheets

(58) Field of Classification Search
CPC ............ G01R 33/0005; G01R 33/0047; G01R 33/0354; G01R 33/34; G01R 33/007
See application file for complete search history.

(56) References Cited

U.S. PATENT DOCUMENTS

| | | | | |
|---|---|---|---|---|
| 2003/0063088 A1* | 4/2003 | Machida | ................ | G01R 33/10 |
| | | | | 345/440 |
| 2013/0090241 A1* | 4/2013 | Harrison | .................. | H01F 6/04 |
| | | | | 324/322 |
| 2015/0226813 A1* | 8/2015 | Yu | ............................ | H05K 7/02 |
| | | | | 324/224 |
| 2015/0268311 A1* | 9/2015 | Yu | ......................... | H01L 23/367 |
| | | | | 505/162 |
| 2015/0327813 A1* | 11/2015 | Fu | .......................... | A61B 5/318 |
| | | | | 600/509 |
| 2016/0017486 A1 | 6/2016 | Yu et al. | | |
| 2016/0174862 A1 | 6/2016 | Yu et al. | | |

FOREIGN PATENT DOCUMENTS

| | | | |
|---|---|---|---|
| JP | 2000051169 A | 2/2000 | |
| JP | 2008-145119 A | 6/2008 | |
| WO | WO-2018007610 A1 * | 1/2018 | ......... A61B 5/04008 |

OTHER PUBLICATIONS

Suzuki et al., Abstract of JP2008145119A; Aug. 26, 2008; obtained from https://worldwide.espacenet.com/.

Office Action, JP Application No. 2023-528507; May 21, 2024; Japan Patent Office, Tokyo, Japan.

* cited by examiner (a)  (b)  (c)

MAGNETOCARDIOGRAPHY MEASURING APPARATUS

CROSS-REFERENCE TO RELATED APPLICATIONS

This application is a continuation of and claims priority to PCT/KR2021/002717 filed on Mar. 5, 2021, which claims priority to Korea Patent Application No. 10-2020-0169438 filed on Dec. 7, 2020, the entireties of which are both hereby incorporated by reference.

TECHNICAL FIELD

The present disclosure relates to a magnetic field measuring apparatus and, more particularly, to a magnetocardiography measuring apparatus provide with a coil in vacuum (CIV).

BACKGROUND

Magnetocardiography (MCG), which is a technique to measure a magnetic field signal generated from ionic current activity of the heart muscle, may be useful for diagnosis of heart disease.

A superconducting quantum interference device (SQUID) is an ultra-sensitive sensor, capable of measuring ultra-low magnetic fields generated in biological activities of heart, brain, nerves and the like. A SQUID sensor operates at low temperature of 4 K or 77 K. Measurement sensitivity is several to tens of fT/√Hz. In general, liquid nitrogen or liquid helium is used to cool the SQUID sensor to a low temperature. A low-temperature refrigerant storage container, capable of storing such a low-temperature refrigerant, is required. The low-temperature refrigerant storage container has a dual structure including a helium internal storage container (a helium tank) storing the low-temperature refrigerant and an external cylinder (a vacuum tank) at room temperature, and a vacuum state is maintained therebetween.

To measure a high-sensitivity signal, it is advantageous to use a SQUID including a low-temperature superconductor. Since niobium (Nb), a super conducting material for use in a low-temperature superconducting SQUID, has a critical temperature of about 9 K, cooling using liquid helium or a low-temperature refrigerator is required. A structure, a thickness, and a mounting method of a thermal insulating material need to be optimized so as to reduce thermal magnetic noise, caused by metal insulation materials (supperinsulation and thermal shield) mounted in a vacuum unit of a Dewar, while reducing an evaporation rate of the Dewar. In addition, since a helium gas is likely to permeate through a small gap, high density of glass fiber reinforced plastic used as a Dewar materials is required.

Since the intensity of a magnetic signal is decreased in inverse proportion to the square of a distance from a magnetic field signal source, a distance between the signal source and a pick-up coil needs to be significantly reduced so as to improve a signal-to-noise ratio (SNR). Research into such a method has been conducted to develop and use a coil-in-vacuum (CIV) SQUID in which a pick-up coil is disposed outside a helium tank, for example, a vacuum unit.

In the case of a CIV SQUID, a pick-up coil and a SQUID sensor are disposed to be maintained in a vacuum state. Accordingly, only a low-temperature refrigerant is present in an internal helium storage container storing a liquefied refrigerant. Accordingly, a neck portion of the internal helium storage container has only to be provided with a path, capable of filling a refrigerant. Accordingly, a diameter of the neck portion may be significantly decreased. As a result, heat flowing through the neck portion may be reduced to decrease an evaporation rate of the liquefied refrigerant.

As heat enters the internal helium storage container, liquid helium is evaporated while boiling. In this case, vibration occurs due to boiling of a liquid in the internal helium storage container. When a pick-up coil is mounted on an external vacuum surface rather than in the internal helium storage container, a vibration effect caused by boiling of the liquid helium may be reduced.

In addition, when a pick-up coil and a SQUID are mounted in vacuum, a cooling rate at the time of initial cooling is reduced as compared with a cooling rate when directly immersed in liquid helium, thereby alleviating rapid contraction stress generated during cooling and removing physical and chemical damages occurring when air or the like, flowing into the internal helium storage container, is adsorbed and condensed to a surface of the SQUID.

SUMMARY

An aspect of the present disclosure is to provide a magnetic field measuring apparatus, capable of easily replacing a SQUID sensor module.

An aspect of the present disclosure is to increase measurement sensitivity of a sensor by reducing vibration occurring when liquid helium boils. In addition, an aspect of the present disclosure is to alleviate stress at the time of cooling a sensor and to improve physical and chemical reliability by mounting the sensor in a vacuum unit.

An aspect of the present disclosure is to provide a cooling device having a neck portion structure having a double-wall structure, capable of blocking radiant heat.

An aspect of the present disclosure is to provide a neck portion having a double-wall structure to provide stability for rotation and tilting of a SQUID sensor module with high load and a liquid helium storage container.

An aspect of the present disclosure is to provide a magnetic field measuring apparatus provided with an evaporated refrigerant collecting tube (a helium gas return tube) having a coaxial dual-tube structure.

An aspect of the present disclosure is to provide a cooling device, capable of recycling a refrigerant.

An aspect of the present disclosure is to provide an effective cooling method of a SQUID sensor module disposed in vacuum.

A magnetic field measuring apparatus according to an example embodiment includes: an external container; an internal container storing a liquid refrigerant, disposed inside the external container, and including a neck portion having a first diameter and a body portion having a second diameter greater than the first diameter, wherein a space between the internal container and the external container is maintained in a vacuum state; a SQUID sensor module mounting plate disposed below the internal container; a plurality of SQUID sensor modules mounted below the SQUID sensor module mounting plate; and a 4K heat shielding portion formed of a conductive mesh disposed to surround the SQUID sensor module mounting plate and the plurality of SQUID sensor modules.

In an example embodiment, the magnetic field measuring apparatus may further include: a main thermal anchor cooled by the refrigerant and disposed on a lower surface of the internal container; a ring-shaped auxiliary thermal anchor coupled to a side surface of the SQUID sensor module mounting plate with the 4K heat shielding portion interposed therebetween and fixing the 4K heat shielding portion; and a litz wire connecting and cooling the main thermal anchor and the auxiliary thermal anchor.

In an example embodiment, the SQUID sensor module mounting plate may be provided with ring-shaped ring dent portion on a lower surface of a side surface of the SQUID sensor module mounting plate. The SQUID sensor module mounting plate may include at least one connection portion penetrating through the SQUID sensor module mounting plate in the ring dent portion. The auxiliary thermal anchor may include at least one projection coupled to the ring dent portion and protruding to be insertable into the connection portion.

In an example embodiment, the 4K heat shielding portion may include: an upper 4K heat shielding portion disposed on an upper surface of the SQUID sensor module mounting plate; and a lower 4K heat shielding portion disposed surround the plurality of SQUID sensor modules. The auxiliary thermal anchor may be coupled to a side surface of the SQUID sensor module mounting plate with the lower 4K heat shielding portion interposed therebetween.

In an example embodiment, the magnetic field measuring apparatus may further include: a sensor guide rod mounted on a lower surface of the internal container, extending through the SQUID sensor module mounting plate, and guiding a vertical motion of the SQUID sensor module mounting plate; and a sensor fixing rod mounted on the lower surface of the internal container and fixed to the SQUID sensor module mounting plate.

In an example embodiment, the SQUID sensor modules may penetrate through the SQUID sensor module mounting plate and are arranged in a first direction and a second direction. Each of the SQUID sensor modules may vertically extend. The magnetic field measuring apparatus may further include a plurality of heat transfer rods extending parallel to the SQUID sensor modules. The heat transfer rods may penetrate through the SQUID sensor module mounting plate, and both ends of the heat transfer rods may each be connected to the 4K heat shielding portion.

In an example embodiment, the SQUID sensor modules may be arranged in a matrix in a first direction and a second direction, perpendicular to the first direction. The SQUID sensor module mounting plate may further include a trench extending in the first direction on the SQUID sensor mounting plate between SQUID sensor modules, arranged in the first direction, and SQUID sensor modules spaced apart from each other in the second direction to be arranged in the first direction.

In an example embodiment, the magnetic field measuring apparatus may further include: signal line connection holes connected to the trench, arranged at regular intervals in the first direction, and penetrating through the SQUID sensor module mounting plate.

In an example embodiment, the SQUID sensor module mounting plate may be provided with a ring-shaped ring dent portion on a lower surface of a side surface of the SQUID sensor module mounting plate. The SQUID sensor module mounting plate may include at least one connection portion penetrating through the SQUID sensor module mounting plate in the ring dent portion. The auxiliary thermal anchor may include at least one projection coupled to the ring dent portion and protruding to be insertable into the connection portion. A trench, disposed on an outermost side in the first direction, may be connected to the connection portion.

In an example embodiment, internal container may include: a neck portion into which a baffle insert is inserted; and a body portion having an increased diameter as compared with the neck portion. The neck portion may have a double-wall structure including an internal cylinder and an external cylinder surrounding the internal cylinder.

In an example embodiment, the internal cylinder may further include a plurality of ring projections protruding outwardly of a cylinder. Thermal anchors may be coupled to the ring projections, respectively. The ring projections may be disposed to be spaced apart from each other. The external cylinder may be separated into external cylinders with the ring projection interposed therebetween.

In an example embodiment, the neck portion may further include a heat shielding layer disposed between the internal cylinder and the external cylinder.

In an example embodiment, an external circumferential surface of the ring projection and an internal circumferential surface of the thermal anchor may be screw-coupled to each other.

In an example embodiment, the thermal anchors may include first to third thermal anchors having a washer shape and vertically spaced apart from each other to be sequentially arranged on an external side of the neck portion. The first thermal anchor may be connected to a 120K heat shielding layer, the second thermal anchor may be connected to an 80K heat shielding layer, the third thermal anchor may be connected to a 40K heat shielding layer, and the 40K heat shielding layer may be disposed to the 4K heat shielding portion.

In an example embodiment, each of the first to third thermal anchors may be provided with a plurality of slits.

In an example embodiment, the magnetic field measuring apparatus may further include: a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. The refrigerant exhaust tube and the refrigerant injection tube may have a coaxial structure, and each of the refrigerant exhaust tube and the refrigerant injection tube may be a dual tube including an internal tube and an external tube.

In an example embodiment, the main thermal anchor may include: a first heat transfer unit formed of oxygen-free copper and including a first disc, and a first lower projection protruding from a central axis of the first disc to a lower surface of the first disc; a second heat transfer unit formed of oxygen-free copper and including a second disc, a second upper projection protruding from a central axis of the second disc to an upper surface of the second disc, and a second lower projection protruding from the central axis of the second disc to a lower surface of the second disc; a third heat transfer unit formed of oxygen-free copper and including a third disc, a third upper projection protruding from a central axis of the third disc to an upper surface of the third disc, and a third lower projection protruding from the central axis of the third disc to a lower surface of the third disc; a fourth heat transfer unit formed of oxygen-free copper and including a fourth disc, a fourth upper projection protruding from an central axis of the fourth disc to an upper surface of the fourth disc, and a fourth lower projection protruding from the central axis of the fourth disc to a lower surface of the fourth disc; a first thermal expansion control unit formed of an insulating material and inserted between the first disc of the first heat transfer unit and the second disc of the second heat transfer unit; and a second thermal expansion control unit formed of an insulating material and inserted between the third disc of the third heat transfer unit and the fourth disc of the fourth heat transfer unit. The second upper projection of the second transfer unit may be provided with a groove for coupling to the first lower projection of the first heat transfer unit. The second lower projection of the second heat transfer unit may have a groove for coupling to the third upper projection of the third heat transfer unit. The third lower projection of the third heat transfer unit may have a groove for coupling to the fourth upper projection of the fourth heat transfer unit.

In an example embodiment, the first thermal expansion control unit may include: a first insulating body portion having the same diameter as a first diameter of the first disc; a second insulating body portion embedded in a lower surface of the internal body and having a second diameter greater than the first diameter; and a third insulating body portion having a third diameter smaller than the second diameter. The third insulating body portion may be disposed to surround an external circumferential surface of the second disc.

In an example embodiment, the SQUID sensor module mounting plate may include a curved portion, and the curved portion may be disposed to surround left ventricle of heart.

In an example embodiment, the internal container may include: a neck portion into which a baffle insert is inserted; and a body portion having an increased diameter as compared with the neck portion. The neck portion may include an internal cylinder portion and an external cylinder portion disposed to surround the internal cylinder portion. The internal cylinder portion may be separated into auxiliary internal cylinders disposed to be vertically spaced apart from each other. Each of the thermal anchors may be inserted between the separated auxiliary internal cylinders.

In an example embodiment, each of the thermal anchors may include: a first cylinder portion having a cylindrical shape; and a first washer portion having a washer shape and connected to an external side of the first cylinder portion from a center of the first cylinder portion. An external side surface of the first cylinder portion may be screw-coupled to an internal side surface of a corresponding auxiliary internal cylinder.

In an example embodiment, the magnetic field measuring apparatus may further include: fixing portions including a second washer portion, having a washer shape, and a second cylinder portion having a cylindrical shape and connected to an internal side surface of the second washer portion. A pair of fixing portions may be disposed on an internal upper surface and an internal lower surface of the first washer portion of the thermal anchor, respectively.

In an example embodiment, the external cylinder portion may include a plurality of auxiliary external cylinder portions disposed to be spaced apart from each other. The auxiliary external cylinder portion may be disposed to surround the second cylinder portion of the fixing portion. A heat shielding layer may be disposed between the auxiliary external cylinder portion and the auxiliary internal cylinder portion.

In an example embodiment, each of the thermal anchors may further include an auxiliary washer portion having a washer shape and connected to an internal side of the first cylinder portion from a center of the first cylinder portion. The auxiliary washer portion may have a slit formed in an azimuthal direction.

In an example embodiment, each of the SQUID sensor modules may include: a cuboidal bobbin, on which a pick-up coil is mounted, having a rectangular cross section; a fixing block connected to the bobbin and inserted in a hole, formed in the SQUID sensor module mounting plate, to be fixed; a SQUID printed circuit board (PCB) mounted on at least one surface, among upper side surfaces of the bobbin, and including a superconducting quantum interference device (SQUID) sensor; and a signal line connection PCB inserted into the fixing block and transferring a signal, detected by the SQUID sensor, to an external circuit.

In an example embodiment, the pick-up coil may be a gradiometer. The pick-up coil may include: a first gradiometer disposed on a first side surface, having a rectangular cross section, of the bobbin; a second gradiometer disposed on a second side surface adjacent to the first side surface of the bobbin; and a third gradiometer disposed on a lower surface of the bobbin.

A magnetic field measuring apparatus according to an example embodiment includes: an external container; and an internal container storing a liquid refrigerant and inserted into the external container. The internal container includes: a neck portion into which a baffle insert is inserted; and a body portion having an increased diameter as compared with the neck portion. The neck portion includes an internal cylinder portion and an external cylinder portion disposed to surround the internal cylinder portion. The internal cylinder portion is separated into auxiliary internal cylinders disposed to be vertically spaced apart from each other. Thermal anchors are each inserted between the separated auxiliary internal cylinders.

In an example embodiment, each of the thermal anchors may include: a first cylinder portion having a cylindrical shape; and a first washer portion having a washer shape and connected to an external side of the first cylinder portion from a center of the first cylinder portion. An external side surface of the first cylinder portion may be screw-coupled to an internal side surface of a corresponding auxiliary internal cylinder.

A SQUID sensor module according to an example embodiment includes: a cuboidal bobbin, on which a pick-up coil is mounted, having a rectangular cross section; a fixing block connected to the bobbin and inserted in a hole, formed in a SQUID sensor module mounting plate, to be fixed; a SQUID printed circuit board (PCB) mounted on at least one surface, among upper side surfaces of the bobbin, and including a superconducting quantum interference device (SQUID) sensor; and a signal line connection PCB inserted into the fixing block and transferring a signal, detected by the SQUID sensor, to an external circuit.

In an example embodiment, the pick-up coil may be a gradiometer. The pick-up coil may include: a first gradiometer disposed on a first side surface of the bobbin having first to fourth side surfaces; a second gradiometer disposed on the second side surface adjacent to the first side surface of the bobbin; and a third gradiometer disposed on a lower surface of the bobbin.

In an example embodiment, the bobbin may include: a lower bobbin having a cuboidal shape; an upper bobbin vertically aligned with the lower bobbin; and a bobbin connection pillar disposed on each of four corners in a vertically extending direction.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
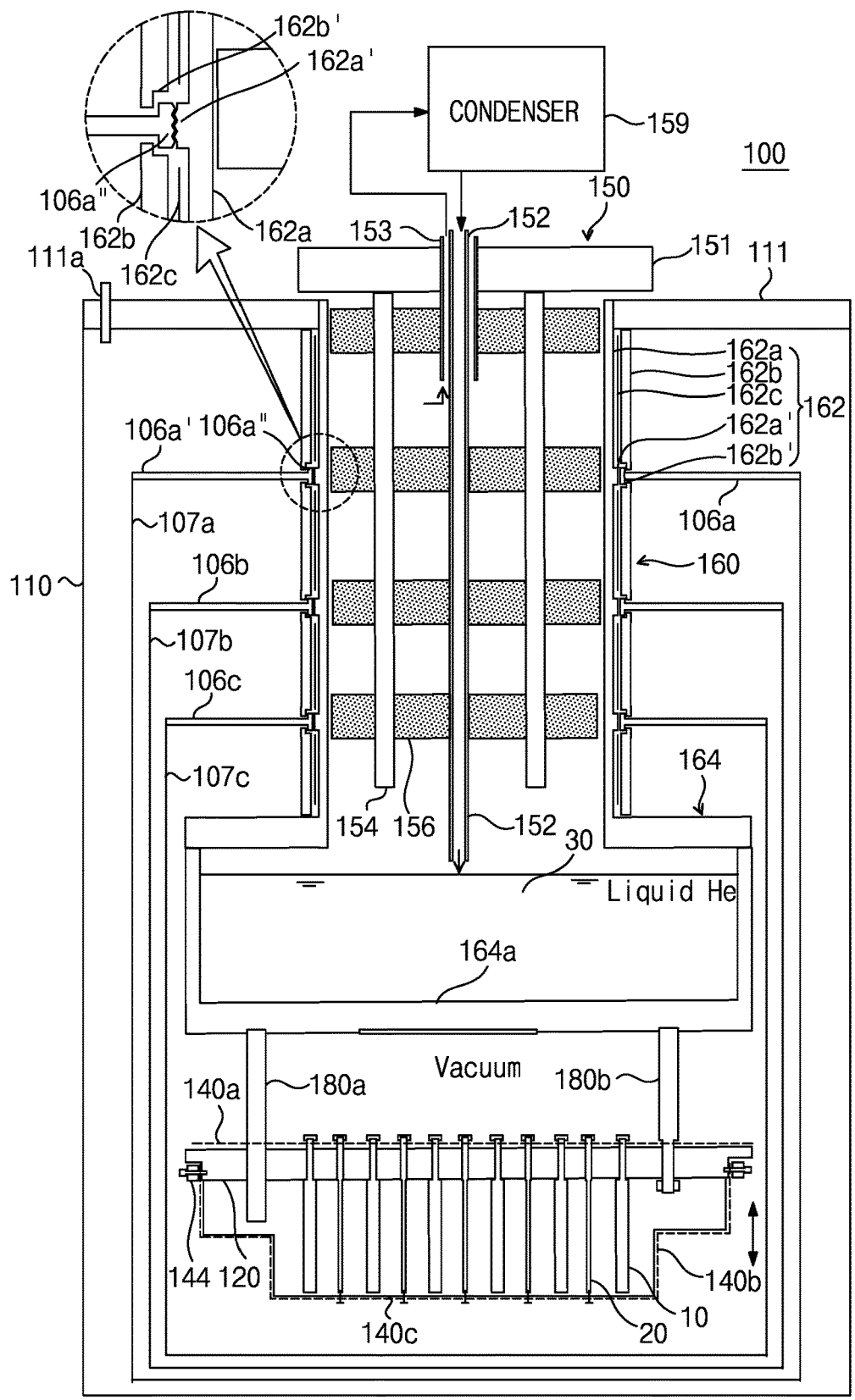
FIGS. 1 and 2 are conceptual diagrams illustrating a magnetic field measuring apparatus according to an example embodiment of the present disclosure.

According to an example embodiment, a technology for directly recondensing a helium gas using a refrigerator and resending the recondensed helium gas to a Dewar is applied. Since magnetic noise and vibration noise caused by the refrigerator and refrigerant delivery tube are significantly large, a special Dewar structure and a special SQUID arrangement method are required to prevent a SQUID from reacting with vibrations.

With the recent increase in the price of helium gas, a technology for directly recondensing a helium gas using a refrigerator and resending the recondensed helium gas to a magnetoencephalography Dewar is required. Evaporated helium is supplied to a refrigerator through a refrigerant exhaust tube, and a liquefied refrigerant is supplied to a Dewar through a refrigerant injection tube. When the refrigerant exhaust tube and the refrigerant injection tube include a single pipe, a refrigerant in the pipe may not be maintained in a cold state due to heat exchange between the inside of the pipe and the outside of the pipe.

A coil-in-vacuum (CIV) SQUID according to an example embodiment addresses an issue regarding ice condensation on a baffle insert lid using a coaxial dual-tube structure. Each of an exhaust tube of a refrigerant-evaporated gas and a refrigerant injection tube has a dual-tube structure. The dual-tube structure may transfer a cold gasified gas to a refrigerator to increase cooling efficiency and to control a rotation and a tilted position of a Dewar.

In the CIV SQUID, a Dewar includes an internal container and an external container surrounding the internal container. However, the internal container absorbs radiant heat externally to increase consumption of a refrigerant.

In the CIV SQUID, the Dewar uses a double-wall structure in a neck portion of the internal container into which a baffle insert is inserted. Such a double-wall structure may make a significant contribution to prevent vacuum break caused by thermal shrinkage of components, constituting an interior of the Dewar, during rapid cooling. In the double-wall structure, a vacuum layer is automatically formed when the interior of the Dewar is cooled and, in order to reduce influx of radiant heat, a heat shielding layer is provided between double walls to significantly reduce influx of radiant heat from a neck of the Dewar. In addition, a dual-vacuum layer may doubly block a micro helium gas, passing through glass fiber reinforced epoxy, such that the degree of vacuum of the vacuum layer may be improved to reduce an evaporation rate of liquefied helium. In the double-wall structure, a thermal anchor is inserted into the internal container to be efficient contact with an evaporated refrigerant. The thermal anchor and the internal container may be screw-coupled to each other to reduce damage caused by expansion between the thermal anchor and the internal container. In addition, the thermal anchor inserted into the double-wall structure may be provided with a plurality of holes to increase a thermal contact surface, and may be in direct contact with the evaporated refrigerant to efficiently use waste heat. Accordingly, an effect of a heat insulation layer may be significantly increased to reduce an evaporation rate of a refrigerant and to stably support an internal structure with a high load. As a result, noise caused by evaporation of the refrigerant and external vibration may be inhibited.

A magnetoencephalography apparatus according to an example embodiment employs a coil-in-vacuum (CIV) SQUID facilitating maintenance of a SQUID sensor, and includes a low-temperature cooling shielding structure to surround SQUID sensors. The low-temperature cooling shielding structures may be disassembled from each other to facilitate the maintenance of the SQUID sensor.

Since the intensity of a magnetic signal from a magnetic field signal source is decreased in inverse proportion to the square of a distance, a distance between the signal source and a pick-up coil needs to be significantly reduced so as to increase a signal-to-noise ratio (SNR). However, when the distance between the signal source and the pick-up coil is significantly small, an evaporation rate of a refrigerant may be increased. Hence, there is a requirement for a device, capable of adjusting the distance between the signal source and the pick-up coil. According to the present disclosure, the distance between the signal source and the pick-up coil may be easily adjusted.

A magnetoencephalography apparatus according to an example embodiment may include a main thermal anchor disposed on a lower surface of an internal container, and the main thermal anchor may include a plurality of heat transfer units screw-coupled to each other and a thermal expansion control unit formed of an insulating material and controlling insulation break caused by thermal expansion between the heat transfer unit and the internal container. When the plurality of heat transfer units are coupled to each other, a pair of thermal expansion control units, disposed to be buried in an external surface and an internal surface of the internal container, may be pressed to inhibit damage to components caused by sealing and thermal expansion.

A SQUID sensor module according to an example embodiment may include a triaxial gradiometer, and may have a structure in which a volume thereof is significantly decreased to reduce thermal capacity. To this end, a gradiometer may be disposed on a bobbin having a cuboidal shape. The bobbin includes an upper bobbin, a lower bobbin, and a bobbin connection pillar. In addition, each of gradiometers constituting the triaxial gradiometer may include a signal coil and a reference coil. The gradiometers may be disposed on different surfaces of a cuboid to be prevented from intersecting each other so as to significantly reduce interference in a single bobbin.

Hereinafter, embodiments of the present disclosure will be described below more fully with reference to accompanying drawings. The present disclosure may, however, be embodied in different forms and should not be construed as limited to the embodiments set forth herein. Rather, these embodiments are provided so that this disclosure will be thorough and complete, and will fully convey the scope of the present invention to those skilled in the art.

Figure 2:
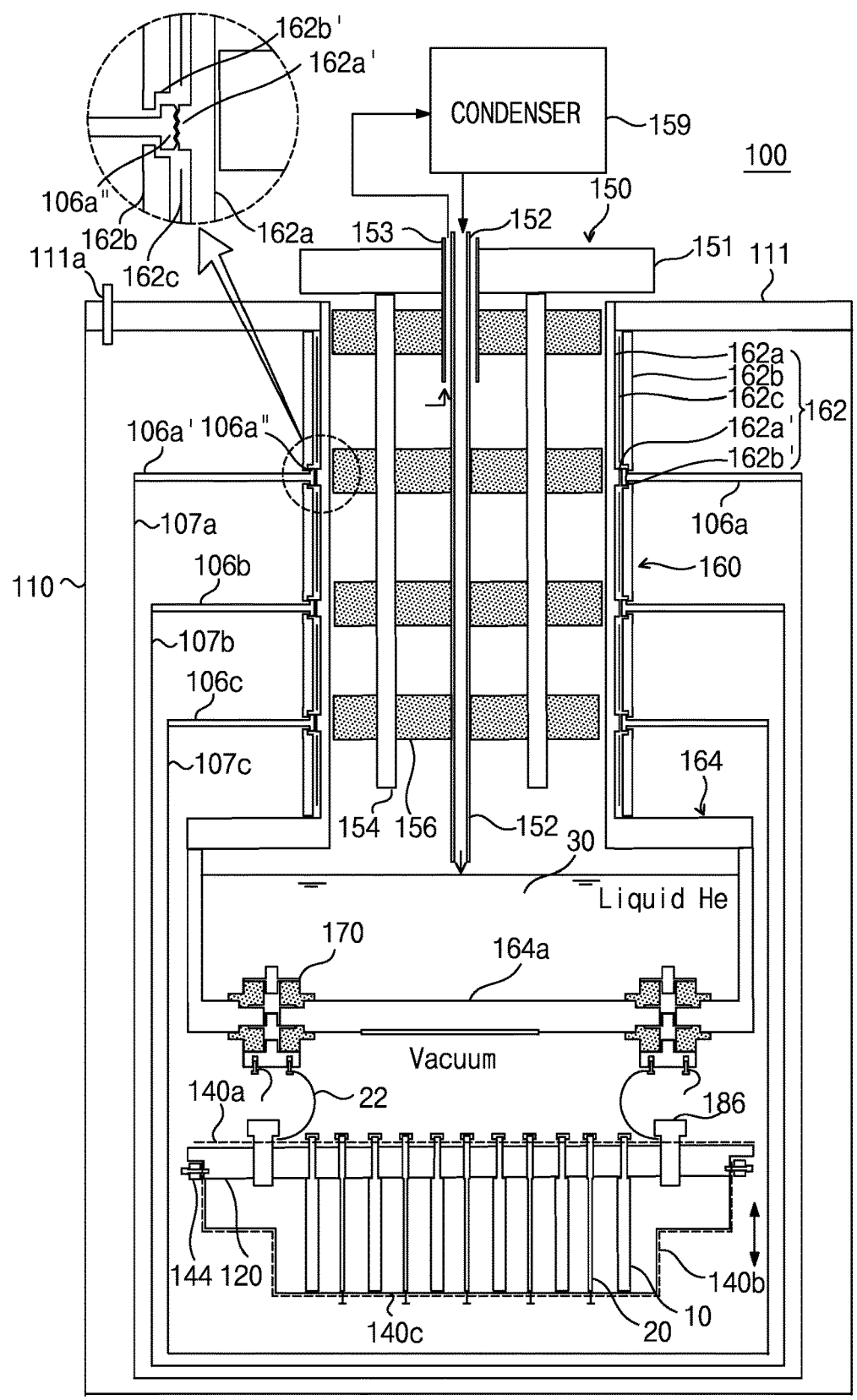

FIGS. 1 and 2 are conceptual diagrams illustrating a magnetic field measuring apparatus according to an example embodiment of the present disclosure.

Figure 3:
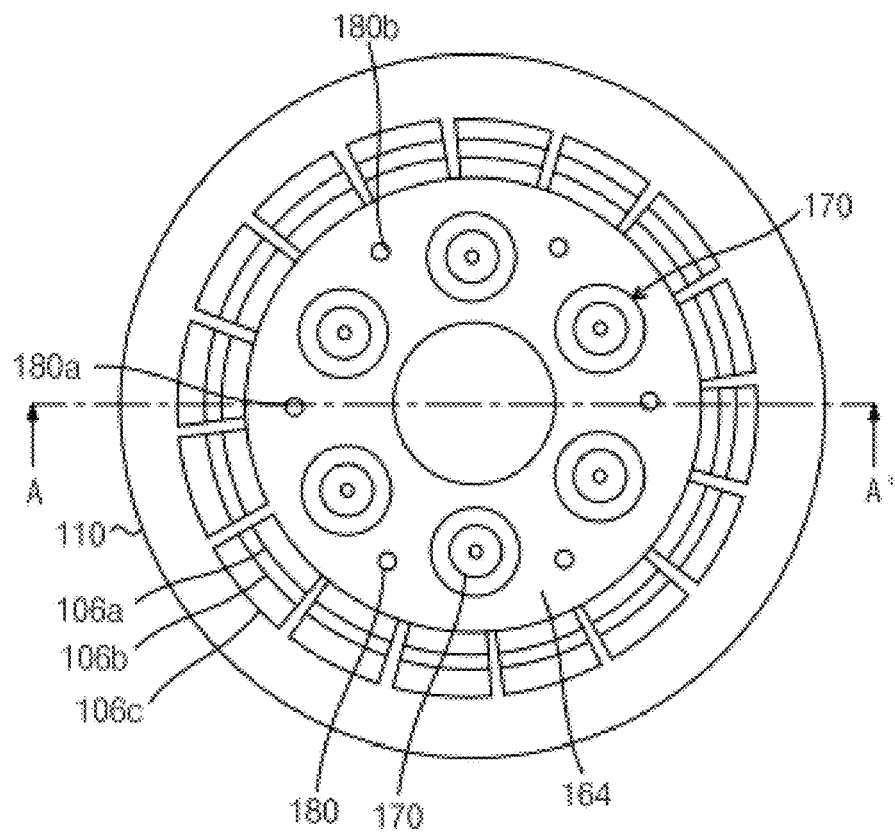
FIG. 3 is a plan view of a lower surface of an internal container viewed in the magnetic field measuring apparatus in FIG. 1.

FIG. 3 is a plan view of a lower surface of an internal container viewed in the magnetic field measuring apparatus in FIG. 1.

Figure 4:
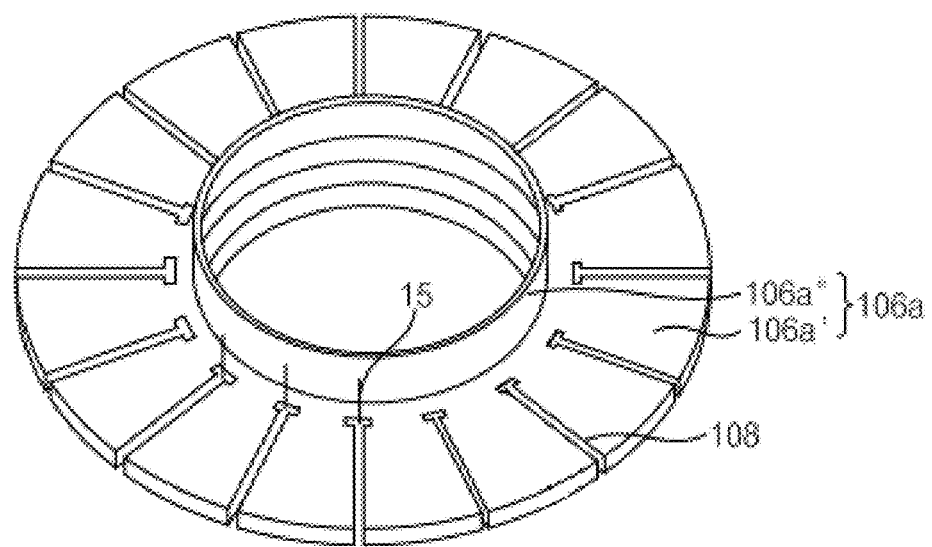
FIG. 4 is a perspective view of a thermal anchor of the magnetic field measuring apparatus in FIG. 1.

FIG. 4 is a perspective view of a thermal anchor of the magnetic field measuring apparatus in FIG. 1.

Figure 5A:
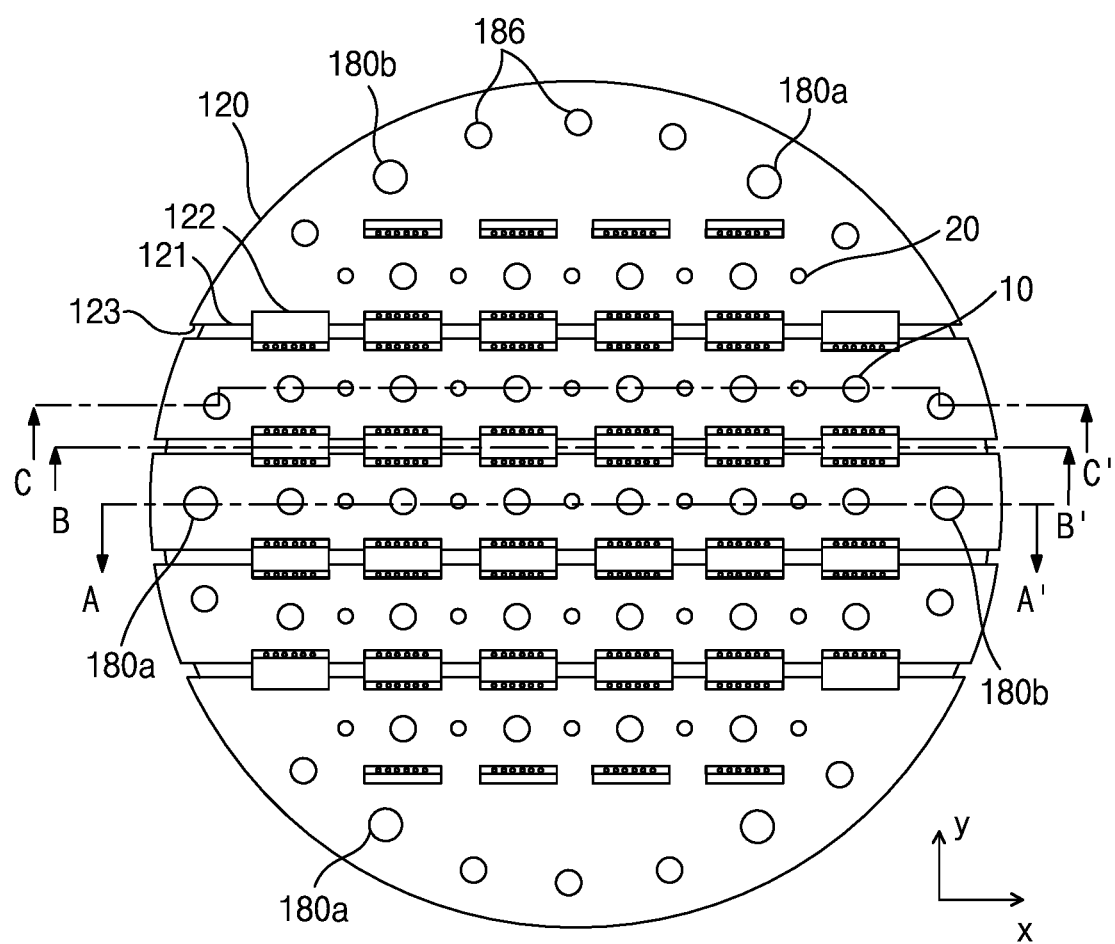
FIG. 5A is a plan view of an upper surface of a SQUID sensor module mounting plate of the magnetic field measuring apparatus in FIG. 1.

FIG. 5A is a plan view of an upper surface of a SQUID sensor module mounting plate of the magnetic field measuring apparatus in FIG. 1.

Figure 5B:
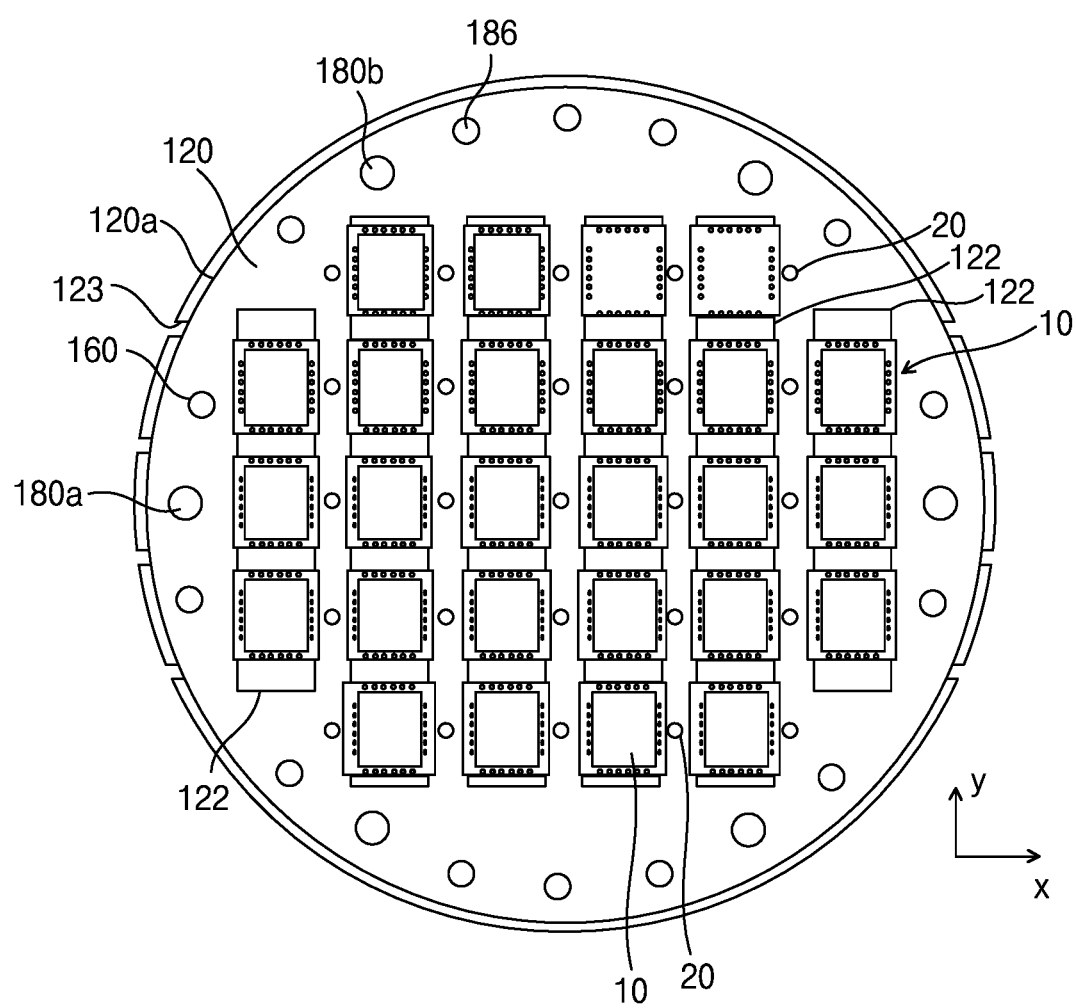
FIG. 5B is a plan view of a lower surface of the SQUID sensor module mounting plate of the magnetic field measuring apparatus in FIG. 1.

FIG. 5B is a plan view of a lower surface of the SQUID sensor module mounting plate of the magnetic field measuring apparatus in FIG. 1.

Figure 6:
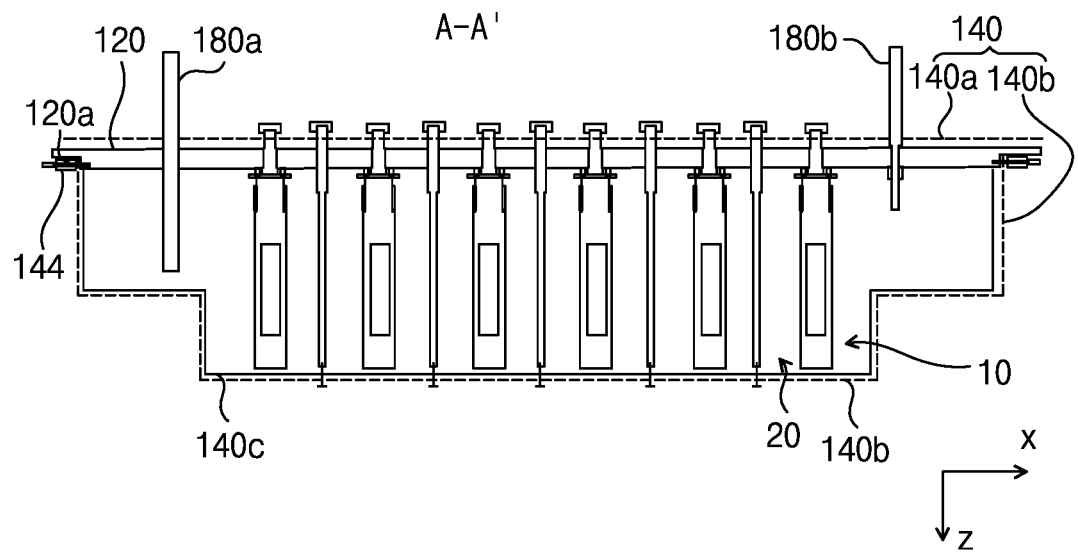
FIG. 6 is a cross-sectional view taken along line A-A' in FIG. 5A.

FIG. 6 is a cross-sectional view taken along line A-A' in FIG. 5A.

Figure 7:
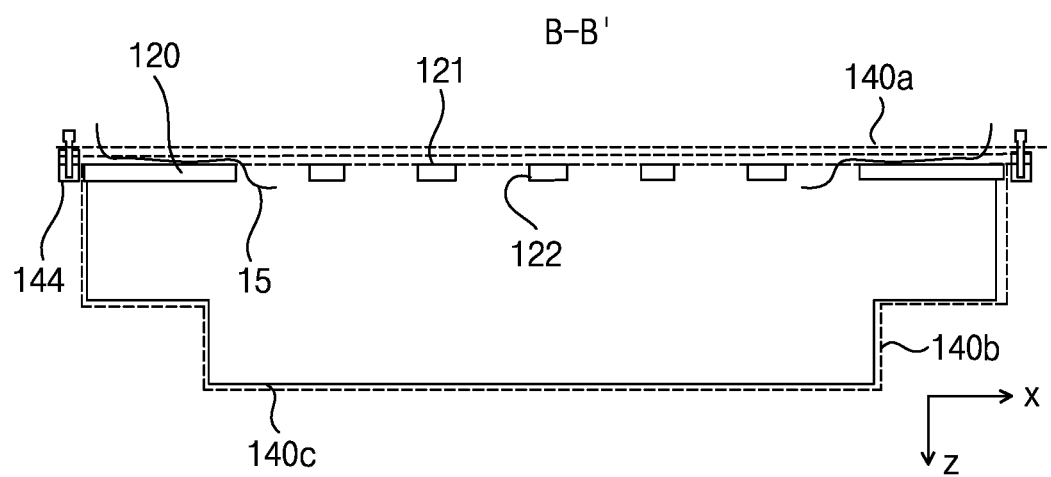
FIG. 7 is a cross-sectional view taken along line B-B' in FIG. 5A.

FIG. 7 is a cross-sectional view taken along line B-B' in FIG. 5A.

Figure 8:
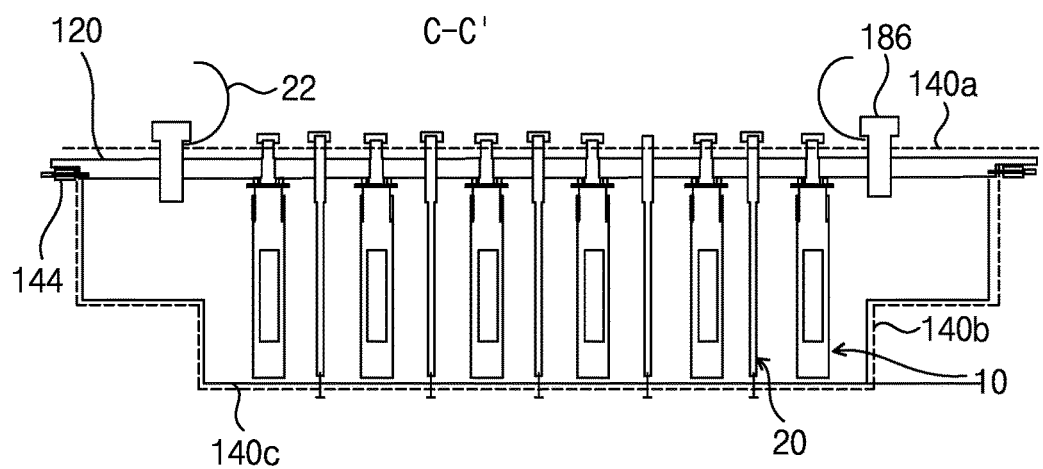
FIG. 8 is a cross-sectional view taken along line C-C' in FIG. 5A.

FIG. 8 is a cross-sectional view taken along line C-C' in FIG. 5A.

Figure 9:
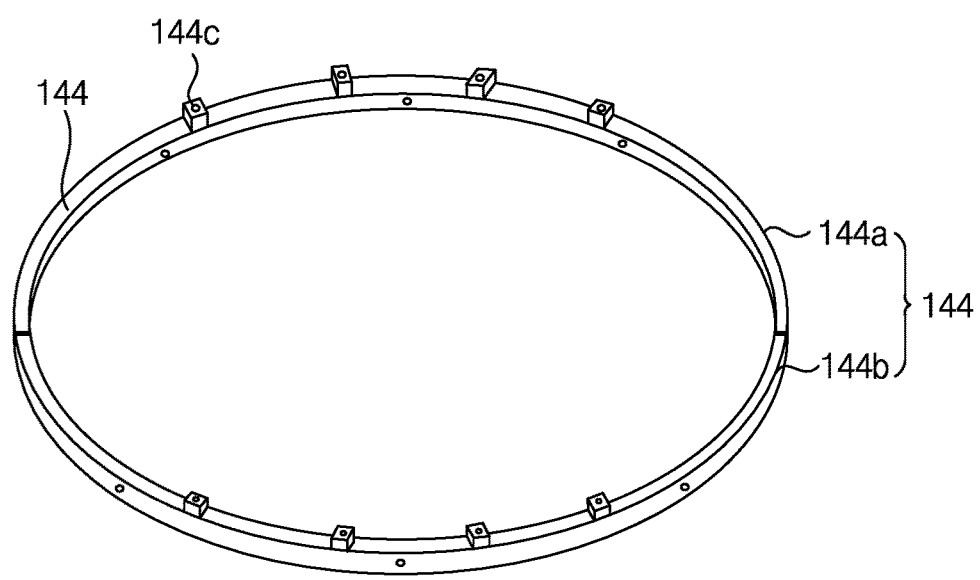
FIG. 9 is a perspective view of an auxiliary thermal anchor in FIG. 1.

FIG. 9 is a perspective view of an auxiliary thermal anchor in FIG. 1.

Referring to FIGS. 1 to 9, a magnetic field measuring device 100 may include an external container 110; an internal container 160 storing a liquid refrigerant 30, disposed inside the external container 110, and including a neck portion 162 having a first diameter and a body portion 164 having a second diameter greater than the first diameter, wherein a space between the internal container 160 and the external container 110 is maintained in a vacuum state; a SQUID sensor module mounting plate 120 disposed below the internal container 160; a plurality of SQUID sensor modules 10 mounted below the SQUID sensor module mounting plate 120; and a 4K heat shielding portion 140 formed of a conductive mesh disposed to surround the SQUID sensor module mounting plate 120 and the plurality of SQUID sensor modules 10.

The external container 110 may have a cylindrical shape and may be a glass fiber reinforced plastic such as G10 epoxy. The external container 110 may include an external container upper plate 111.

The internal container 160 may store the liquid refrigerant 30, and may cool the SQUID sensor module 10 through a main thermal anchor 170 and the litz wire 22. A material of the internal container 160 may be a glass fiber reinforced plastic such as G10 epoxy. The internal container 160 may include a neck portion 162, into which a baffle insert 150 is inserted, and a body portion 164 having an increased diameter as compared with the neck portion 162. The neck portion 162 may have a double-wall structure including an internal cylinder and an external cylinder surrounding the internal cylinder. The neck portion 162 may include an internal cylinder 162a and an external cylinder 162b surrounding the internal cylinder 162a. A heat shielding layer 162c may be disposed between the internal cylinder 162a and the external cylinder 162b. The heat shielding layer 162c may have a multilayer structure in which a metal thin film having high reflectivity and low emissivity and an ultrathin non-woven fabric having low thermal conductivity are sequentially stacked.

The internal cylinder 162a may further include a plurality of ring projections 162a' protruding outwardly of a cylinder. The ring projection 162a' may have a cylindrical ring shape, and may be formed to be integrated with the internal cylinder 162a. A screw for screw coupling may be formed on an external circumferential surface of the ring projection 162a'.

The thermal anchors 106a to 106c may be coupled to the ring projections 162a', respectively. The ring projections 162a' may be spaced apart from each other, and the external cylinder 162b may be separated from each other with the ring projection 162a' interposed therebetween. The external circumferential surface of the ring projection 162a' and internal circumferential surfaces of the thermal anchors 106a to 106c may be screw-coupled to each other.

The ring projections 162a' may be disposed to be spaced apart from each other. The external cylinder 162b may be separated from each other with the ring projection 162a' interposed therebetween. For example, the external cylinder 162b may include a plurality of cylindrical portions separated from each other. A distance between the external cylinder 162b and the internal cylinder 162a may be within several millimeters (mm). Each of the external cylinders 162a may include a thermal anchor coupling portion 106a" and a raised portion 162b' to surround the ring projection 162a'. After the external cylinder 162b is coupled to surround the ring projection 162a', a coupling portion may be fixed and sealed with an adhesive such as epoxy.

The thermal anchors 106a to 106c may include washer-shaped first to third thermal anchors 106a to 106c vertically spaced apart from each other and sequentially disposed outside the neck portion 162. Each of the first to third thermal anchors 106a to 106c may have a plurality of slits 108 extending in a radial direction.

The first thermal anchor 106a may be connected to a 120K heat shielding layer 107a, the second thermal anchor 106b may be connected to an 80K heat shielding layer 107b, and the third thermal anchor 106c may be connected to a 40K heat shielding layer 107c. The 40K heat shielding layer 107c may be disposed to surround the 4K heat shielding portion 140. The 80K heat shielding layer 107b may be disposed to surround the 40K heat shielding layer 107c. The 120K heat shielding layer 107a may be disposed to surround the 80K heat shielding layer 107b.

The thermal anchors 106a, 106b, and 106c may be coupled to the ring projections 162a', respectively. An external circumferential surface of the ring projection 162a' and internal circumferential surfaces of the thermal anchors 106a, 106b, and 106c may be screw-coupled to each other. Each of the thermal anchors 106a, 106b, and 106c may have a circular washer shape. The thermal anchors 106a, 106b, and 106c may be copper or aluminum.

The thermal anchor 106a may include a cylindrical thermal anchor coupling portion 106a" and a disk-shaped thermal anchor body 106a' disposed on an external circumferential surface of a thermal anchor coupling portion. An internal circumferential surface of the thermal anchor coupling portion 106a" may be screw-coupled to an external circumferential surface of the ring projection 162a'. Accordingly, the thermal anchors 106a, 106b, and 106c may be stably fixed to the internal container 160, and may be cooled while being in thermal contact with each other in large areas. The screw-coupling of the ring projection 162a' and the thermal anchor 106a may improve mechanical stability while providing efficient thermal contact brought by thermal expansion.

The double-wall structure may block influx of radiant heat into the internal container 160 from an external entity. When the internal container 160 is cooled by a refrigerant, a space between the internal cylinder and the external cylinder may be maintained in a vacuum state. Accordingly, heat influx caused by heat transfer may be blocked, and the heat shielding layer 162c may additionally block influx of radiant heat. As a result, a neck portion of the double-wall structure may provide higher mechanical stability and higher heat shielding efficiency than a neck portion of a single-wall structure.

The thermal anchors 106a, 106b, and 106c may include first to third thermal anchors 106a, 106b, and 106c arranged in the order named. The first thermal anchor 106a may be disposed on an uppermost side of the neck portion 362, and may be connected to the 120K heat shielding layer 107a. The second thermal anchor 106b may be disposed below the first thermal anchor 106a, and may be connected to the 80K heat shielding layer 107b. The third thermal anchor 106c may be disposed below the second thermal anchor 106b, and may be connected to the 40K heat shielding layer 107b. An external diameter of the first thermal anchor 106a may be greater than an external diameter of the second thermal anchor 106b.

The first thermal anchor 106a may be farthest spaced apart from the refrigerant to be maintained at highest temperature, whereas the third thermal anchor 106c may be closest to the refrigerant to be maintained at lowest temperature. The first to third thermal anchors 106a, 106b, and 106c may be brought into thermal contact an evaporated refrigerant to be cooled.

The 40K heat shielding layer 107c may be coupled to an external circumferential surface of the third thermal anchor 106c, may be disposed to surround the internal container 260 and to block the influx of radiant heat. The 40K heat shielding layer 107c may include a metal mesh, woven with metal wires insulated from each other, and a heat insulation film. The 40K heat shielding layer 107c may surround the 4K heat shielding portion 140.

The 80K heat shielding layer 107b may be coupled to an external circumferential surface of the second thermal anchor 106b, and may be disposed to surround the 40K heat shielding layer 107a and to block the influx of radiant heat. The 80K heat shielding layer 107b may include a metal mesh, woven with metal wires insulated from each other, and a heat insulation film. The 80K heat shielding layer 107b may surround the 4K heat shielding portion 140.

The 120K heat shielding layer 107a may be coupled to an external circumferential surface of the first thermal anchor 106a, and may be disposed to surround the 80K heat shielding layer 107b and to block the influx of radiant heat. The 120K heat shielding layer 107a may include a metal mesh, woven with metal wires insulated from each other, and a heat insulation film. The 120K heat shielding layer 107a may surround the 80K heat thermal layer 107b.

The space between the internal container 160 and the external container 110 may be maintained in a vacuum state. An external container lid 111 may include an exhaust port 111a connected to a vacuum pump. The exhaust port 111a may be formed of a G10 epoxy tube. A lower surface 164a of the body portion 164 may have a plurality of getter grooves. A getter, collecting residual gases in a vacuum state, may be disposed in the getter groove.

The baffle insert 150 may be disposed to be inserted into the neck portion 162 of the internal container 160. The baffle insert 150 may include an insert upper plate 151, a baffle 156 disposed below the insert upper plate 151, and a plurality of guide rods 154 supporting the baffle 156 and fixed to the insert upper plate 151.

The insert upper plate 151 may have a disc shape, and may be formed of G10 epoxy. The insert upper plate 151 may be fixed to the external container lid 111. The guide rod 154 may be formed of G10 epoxy, and may have a rod shape or a pipe shape. The guide rod 154 may support the baffle 156. The baffle 156 may include Styrofoam having improved warmth retention and a conductive plate. The conductive plate may include an aluminum-coated Mylar layer and a copper layer sequentially stacked to block the radiant heat.

A refrigerant exhaust tube 153 may be disposed on the insert upper plate 151 of the baffle insert 150, and may exhaust an evaporated refrigerant. A refrigerant injection tube 152 may be disposed on the insert upper plate 151 of the baffle insert 150, and may inject a refrigerant. Each of the refrigerant exhaust tube 153 and the refrigerant injection tube 152 may have a dual-tube structure including an internal tube and an external tube. In the dual-tube structure, a space between the internal tube and the external tube may be maintained in a vacuum state during cooling. The refrigerant injection tube 152 may have a coaxial structure inserted into the refrigerant exhaust tube 153. The refrigerant exhaust tube 153 and the refrigerant injection tube 152 may be formed of G10 epoxy.

Coaxial dual tubes 152 and 153 may reduce thermal contact with the insert upper plate 151 to reduce ice formation of the insert upper plate 151. When the refrigerant exhaust tube and the refrigerant injection tube are a single tube, the refrigerant exhaust tube 153 and the refrigerant injection tube 152 may form ice to impede sealing of the external container lid 111 and the insert upper plate 151 and to increase influx of external heat. The coaxial dual tubes 152 and 153 may be disposed on a central axis of the insert upper plate 151. One end of the refrigerant exhaust tube 153 may be disposed in a higher location than the first thermal anchor 106a.

A condenser 159 may be connected to the refrigerant exhaust tube 153 and the refrigerant injection tube 152, and may condense an evaporated refrigerant exhausted through the refrigerant injection tube 153. The condenser 159 may be disposed outside a magnetically shielded room.

A signal line connection box may be disposed outside the external container 110, and may connect signal lines 15 of the SQUID sensor to each other.

The main thermal anchor 170 may be cooled by the refrigerant, and may be disposed on a lower surface of the internal container 160 at regular intervals on a constant circumference. The number of main column anchors 170 may be six.

Figure 10:
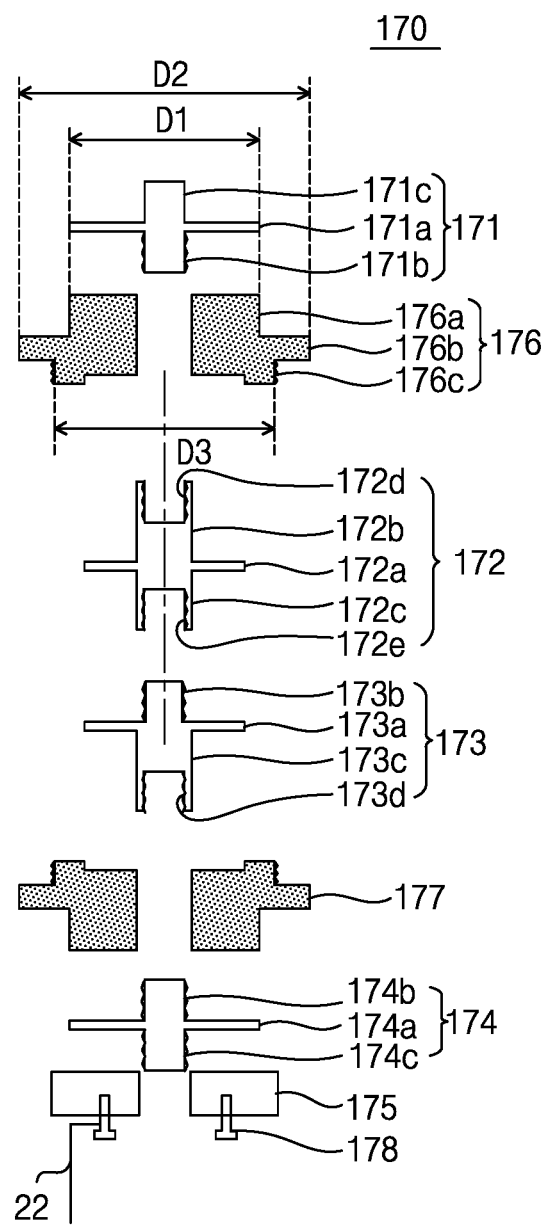
FIG. 10 is a cross-sectional view of a main thermal anchor according to an example embodiment of the present disclosure.

FIG. 10 is a cross-sectional view of a main thermal anchor according to an example embodiment of the present disclosure.

A main thermal anchor 170 may include a first heat transfer unit 171, a second heat transfer unit 172, a third heat transfer unit 173, a fourth heat transfer unit 174, a fifth heat transfer unit 175, a first thermal expansion control unit 176, and a second thermal expansion control unit 177. The main thermal anchor 170 may include of a plurality of components to increases a thermal contact area while inhibiting damage to the internal container caused by thermal expansion, and thus, may efficiently cool a litz wire 12 and a SQUID sensor.

The first thermal expansion control unit 176 may be coupled to a dual groove having two radii and formed on an internal side of a lower surface of an internal container, and the second thermal expansion control unit 177 may be coupled to a dual groove having two radii and formed on an external side of the lower surface of the internal container.

The first heat transfer unit 171 may be formed of oxygen-free copper and may include a first disc 171a, and a first lower projection 171b protruding from a central axis of the first disc 171a to a lower surface of the first disc 171a. The first heat transfer unit 171 may further include a first upper projection 171c protruding from the central axis of the first disc 171a to an upper surface of the first disc 171a.

The second heat transfer unit 172 may be formed of oxygen-free copper, and may include a second disc 172a, a second upper projection 172b protruding from a central axis of the second disc 172a to an upper surface of the second disc 172a, and a second lower projection 172c protruding from the central axis of the second disc 172a to a lower surface of the second disc 172a. The second upper projection 172b of the second heat transfer unit 172 may have a screw groove 172d for coupling to the first lower projection 171b of the first heat transfer unit 171. The second lower projection 172c of the second heat transfer unit 172 may have a screw groove 172e for coupling to the third upper projection 173b of the third heat transfer unit 173.

The third heat transfer unit 173 may be formed of oxygen-free copper, and may include a third disc 173a, a third upper projection 173b protruding from a central axis of the third disc 173a to an upper surface of the third disc 173a, and a third lower projection 173c protruding from the central axis of the third disc 173a to a lower surface of the third disc 173a. The third lower projection 173c of the third heat transfer unit 173 may have a screw groove 173d for coupling to a fourth upper projection 174b of the fourth heat transfer unit 174.

The fourth heat transfer unit 174 may be formed of oxygen-free copper, and may include a fourth disc, a fourth upper projection 174b protruding from an central axis of the fourth disc to an upper surface of the fourth disc, and a fourth lower projection 174c protruding from the central axis of the fourth disc to a lower surface of the fourth disc.

The fifth heat transfer unit 175 may be formed of oxygen-free copper, and may include a disc. The fifth heat transfer unit 175 may be coupled to the fourth lower projection 174c of the fourth heat transfer unit 174. A lower surface of the fifth heat transfer unit 175 may be coupled to a fixing means 178. The fixing means 178 may fix and cool a litz wire 22.

The first thermal expansion control unit 176 may be formed of an insulating material, and may be inserted between the first disc 171a of the first heat transfer unit 171 and the second disc 172b of the second heat transfer unit 172. The first thermal expansion control unit 176 may be formed of the same material as the internal container 160.

The second thermal expansion control unit 177 may be formed of an insulating material, and may be inserted between the third disc 173a of the third heat transfer unit 173 and the fourth disc 174a of the fourth heat transfer unit 174. The second thermal expansion control unit 177 may be formed of the same material as the internal container 160.

The first thermal expansion control unit 176 may include a first insulating body portion 176a having the same diameter as a first diameter D1 of the first disc 171a, a second insulating body portion 176b embedded in a lower surface of the internal body and having a second diameter D2 greater than the first diameter D1, and a third insulating body portion 176c having a third diameter D3 smaller than the second diameter D2. The third insulating body portion 176c may be disposed to cover an external circumferential surface of the second disc 172a. The external circumferential surface of the third insulating body portion 176c may have a screw groove.

The second thermal expansion control unit 177 may have the same structure as the first thermal expansion control unit 176.

When the first to fourth heat transfer units 171 to 174 are coupled to each other, the first thermal expansion control unit 176 and the second thermal expansion control unit 177 may be pressed to be sealed with the internal container. In addition, the first disc 171a and the fourth disc 174a may be sealed by pressing the first thermal expansion control unit 176 and the second thermal expansion control unit 177.

The main thermal anchor 170 may cool the 4K heat shielding portion and the SQUID sensor modules 10 through litz wires.

Returning to FIG. 1, a sensor guide rod 180a may be mounted on the lower surface 164a of the internal container, and may extend through the SQUID sensor module mounting plate 120 to guide a vertical motion of the SQUID sensor module mounting plate 120. The sensor guide rod 180a may be periodically disposed on a circumference having a certain radius on the lower surface 164a of the internal container 160.

A sensor fixing rod 180b may be mounted on the lower surface 164a of the internal container 160, and may be fixed to the SQUID sensor module mounting plate 120. The sensor fixing rod 180b may be periodically disposed on a circumference having a certain radius on the lower surface 164a of the internal container 160. A length or a fixed position of the sensor fixing rod 180b may be adjusted to adjust a distance between a magnetic field signal source and a pick-up coil.

The SQUID sensor module mounting plate 120 may have a disc shape, and may be a non-magnetic material such as G10 epoxy. The SQUID sensor module mounting plate 120 may include a ring-shaped ring dent portion 120a on a lower surface of a side surface of the SQUID sensor module mounting plate 120. The SQUID sensor module mounting plate 120 may include at least one connection portion 123 penetrating through the SQUID sensor module mounting plate 120 in the ring dent portion 120a.

The SQUID sensor modules 10 may penetrate through the SQUID sensor module mounting plate 120 and may be arranged in a first direction (an x-axis direction) and a second direction (a y-axis direction). Each of the SQUID sensor modules 10 may vertically extend. Specifically, the SQUID sensor modules 10 may be arranged in a matrix in the first direction and the second direction. An upper surface of the SQUID sensor module mounting plate 120 may has a trench 121 extending from the SQUID sensor module mounting plate 120 in the first direction between SQUID sensor modules, arranged in the first direction, and SQUID sensor modules spaced apart from each other in the second direction to be arranged in the first direction. A signal line connection hole 122 may be connected to the trench 121 and arranged at regular intervals in the first direction, and may penetrate through the SQUID sensor module mounting plate 120. The signal line connection hole 122 and the trench 121 may provide a connection path for signal lines of a plurality of SQUID sensors constituting the SQUID sensor module 10.

An auxiliary thermal anchor 144 includes at least one projection 144c coupled to the ring dent portion 120a and protruding to be insertable into the connection portion 123, and the trench 121 disposed on an outermost side in the first direction may be connected to the connection portion 123.

The auxiliary thermal anchor 144 may be in the form of a ring coupled to a side surface of the SQUID sensor module mounting plate 120 with the 4K heat shielding portion 140 interposed therebetween and fixing the 4K heat shielding portion 140. The auxiliary thermal anchor 144 may be brought into thermal contact with the 4K heat shielding portion 140 to cool the 4K heat shielding portion 140. The auxiliary thermal anchor 144 may be formed of oxygen-free copper, and may be separated into a first auxiliary thermal anchor 144a and a second auxiliary thermal anchor 144b, having a semicircular shape, to inhibit the flow of vortex.

The 4K heat shielding portion 140 may include an upper 4K heat shielding portion 140a, disposed on the upper surface of the SQUID sensor module mounting plate 120, and a lower 4K heat shielding portion 140b disposed to surround the plurality of SQUID sensor modules 10. The auxiliary thermal anchor 144 may be coupled to a side surface of the SQUID sensor module mounting plate 120 through the lower 4K heat shielding portion 140b. The lower 4K heat shield 140b may be disposed to surround a 4K heat shielding housing 140c. The 4K heat shielding housing 140c may be formed of a thin plastic material. The 4K heat shielding housing 140c may have at least one opening for evacuation. The 4K heat shield housing 140c may have a raised portion while extending in a vertical direction to have a small diameter in a region, in which the SQUID sensor modules 10 are disposed, so as to reduce a cooling space.

A plurality of heat transfer fixing portion 186 may be periodically mounted along an edge of the SQUID sensor module mounting plate 120. The heat transfer fixing portions 186 may include a metal such as oxygen-free copper having a high heat transfer rate. The plurality of heat transfer fixing portions 186 may be in thermal contact with the main thermal anchor 170 through a litz wire, and may cool the upper 4K heat shield portion 140a while fixing the upper 4K heat shield portion 140a and may be fixed to the SQUID sensor module mounting plate 120. For example, a single main thermal anchor 170 may be connected to a plurality of heat transfer fixing portions 186 through litz wires. The litz wire 22 may include a plurality of flexible copper wires.

A plurality of heat transfer rods 20 may be fixed to the SQUID sensor module mounting plate 120, and may extend parallel to the SQUID sensor modules 10. The plurality of heat transfer rods 20 may be arranged in a matrix. The heat transfer rods 20 may penetrate through the SQUID sensor module mounting plate 120, and both ends of the heat transfer rods 29 may be connected and fixed to be in thermal contact with the 4K heat shielding portion 140.

Each of the SQUID sensor modules 10 may be cooled by the 4K heat shielding portion 140. A space between the external container 110 and the internal container 160 is in a vacuum state. The magnetic field measuring apparatus 100 may measure magnetocardiography, and may be disposed inside a magnetically shielded room.

When some of the SQUID sensor modules 10 fail, the SQUID sensor modules 10 may be separated to be replaced. To this end, the auxiliary thermal anchor 144 may removed from the SQUID sensor module mounting plate 120, and then the 4K heat shielding portion 140 may be removed. Accordingly, a failed SQUID sensor module may be easily replaced.

Figure 11:
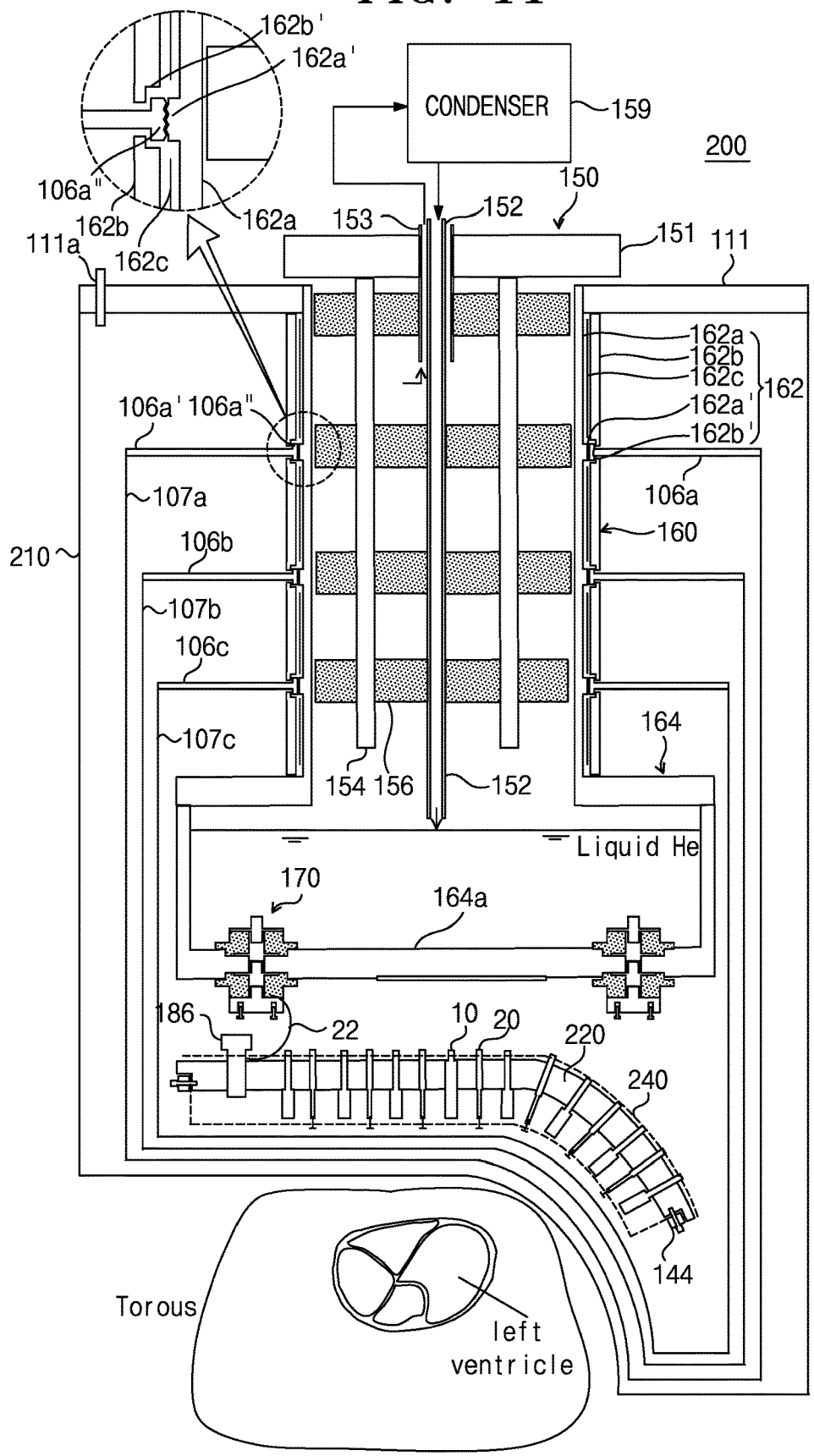
FIG. 11 is a conceptual diagram illustrating a magnetic field measuring apparatus according to another example embodiment of the present disclosure.

FIG. 11 is a conceptual diagram illustrating a magnetic field measuring apparatus according to another example embodiment of the present disclosure.

Figure 12:
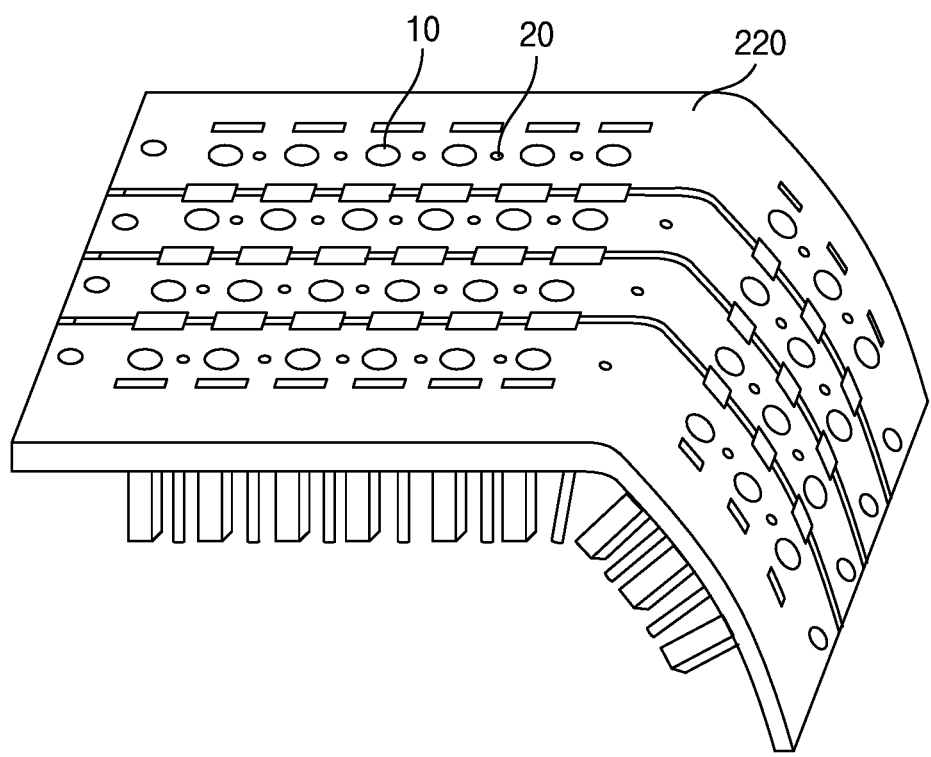
FIG. 12 is a perspective view of a SQUID sensor mounting plate in FIG. 11.

FIG. 12 is a perspective view of a SQUID sensor mounting plate in FIG. 11.

Referring to FIGS. 11 and 12, a magnetic field measuring apparatus 200 may include an external container 210; an internal container 160 storing a liquid refrigerant 30, disposed inside the external container 210, and including a neck portion 162 having a first diameter and a body portion 164 having a second diameter greater than the first diameter; a SQUID sensor module mounting plate 220 disposed in a space maintained in a vacuum state between the internal container 160 and the external container 210; a plurality of SQUID sensor modules 10 mounted below the SQUID sensor module mounting plate 220; and a 4K heat shielding portion 240 formed of a conductive mesh disposed to surround the SQUID sensor module mounting plate 220 and the plurality of SQUID sensor modules 10.

An upper portion of the external container 210 may have a cylindrical shape, but the lower portion thereof may be curved to cover a part of a human body. Accordingly, the SQUID sensor module may cover a side of the left breast to measure a magnetic field signal of the left ventricle of heart.

The SQUID sensor module mounting plate 220 may be a circular plate or a rectangular plate bent in a C shape or an L shape. The plurality of SQUID sensor modules 10 and the plurality of heat transfer rods 20 may be arranged in a matrix. The SQUID sensor module mounting plate 220 may include a curved portion. The curved portion may be arranged to surround the left ventricle of heart.

The 4K heat shielding portion 240 may be disposed to surround the SQUID sensor modules 10 and the SQUID sensor module mounting plate 220. The 4K heat shielding portion 240 may be cooled by the main thermal anchor and a litz wire.

Figure 13:
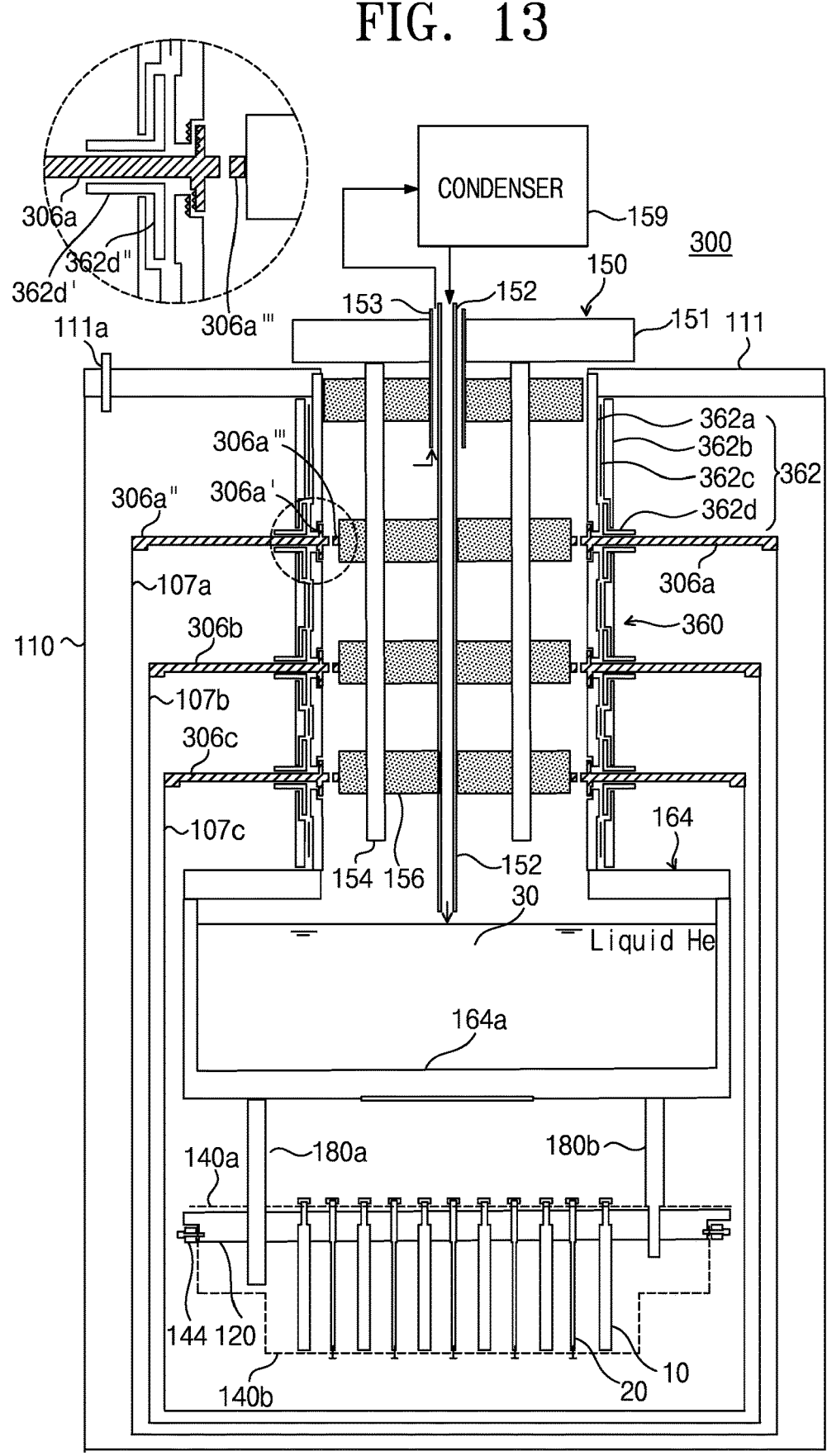
FIG. 13 is a conceptual diagram illustrating a magnetic field measuring apparatus according to another example embodiment of the present disclosure.

FIG. 13 is a conceptual diagram illustrating a magnetic field measuring apparatus according to another example embodiment of the present disclosure.

Figure 14:
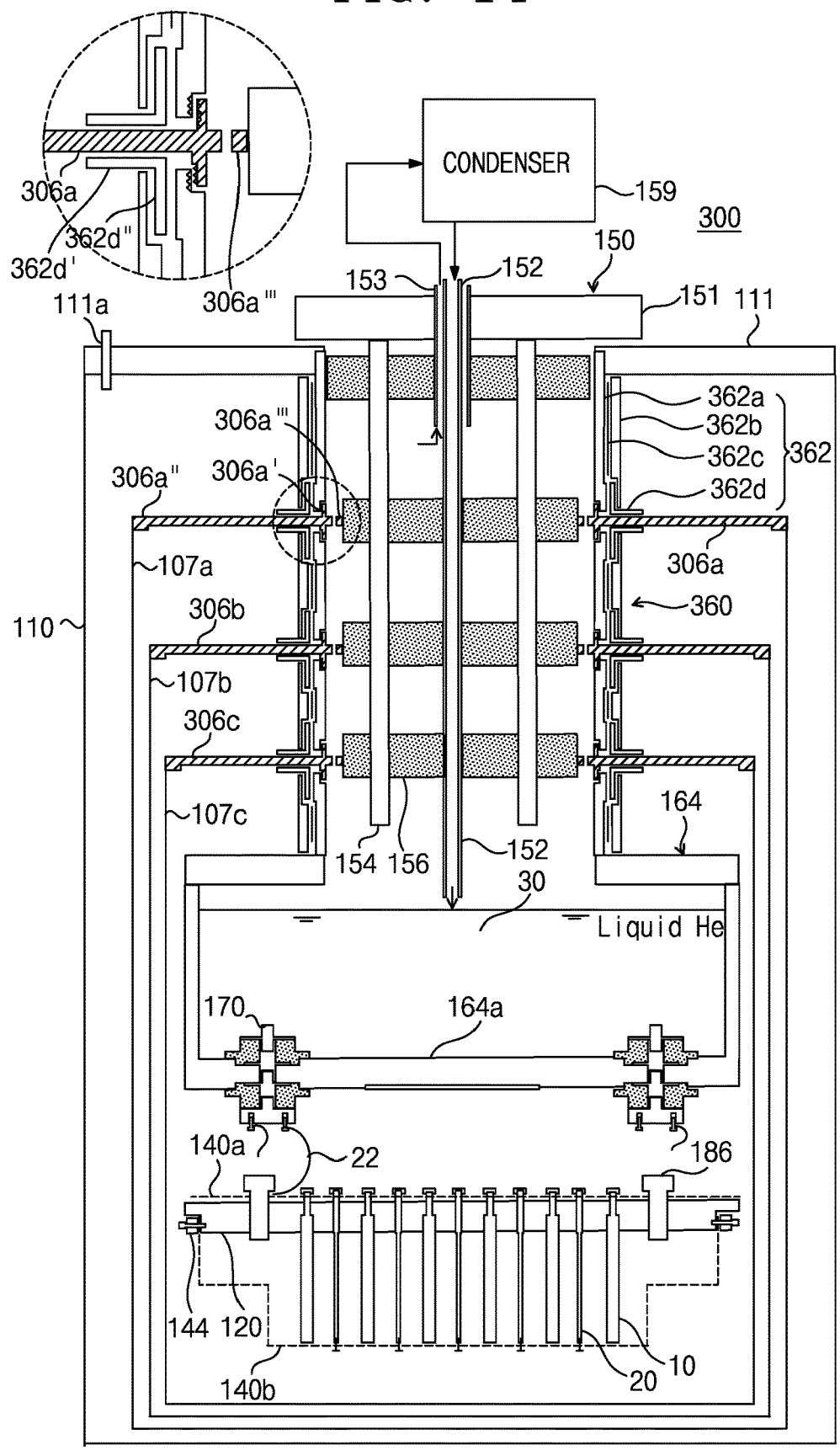
FIG. 14 is a cross-sectional view of the magnetic field measuring apparatus in FIG. 13.

FIG. 14 is a cross-sectional view of the magnetic field measuring apparatus in FIG. 13.

Referring to FIGS. 13 and 14, a magnetic field measuring apparatus 300 may include an external container 110; an internal container 360 storing a liquid refrigerant 30, disposed inside the external container 110, and including a neck portion 362 having a first diameter and a body portion 364 having a second diameter greater than the first diameter; a SQUID sensor module mounting plate 120 disposed in a space maintained in a vacuum state between the internal container 360 and the external container 110; a plurality of SQUID sensor modules 10 mounted below the SQUID sensor module mounting plate 120; and a 4K heat shielding portion 140 formed of a conductive mesh disposed to surround the SQUID sensor module mounting plate 120 and the plurality of SQUID sensor modules 10.

The internal container 360 may include a neck portion 362, into which a baffle insert 150 is inserted, and a body portion 164 having an increased diameter as compared with the neck portion 362. The neck portion 362 may include an internal cylinder portion 362a and an external cylinder portion 362b disposed to surround the internal cylinder portion 362a. The internal cylinder portion 362a may be separated into auxiliary internal cylinders disposed to be vertically spaced apart from each other. Thermal anchors 306a, 306b, and 306c may be each inserted between the separated auxiliary internal cylinders.

Each of the column anchors 306a, 306b, and 306c includes a first cylinder portion 306a', having a cylindrical shape, and a first washer portion 306a" having a washer shape and connected to an external side of the first cylinder portion 306a' from a center of the first cylindrical portion 306a'. An external side surface of the first cylinder portion 306a' may be screw-coupled to an internal surface of a corresponding auxiliary internal cylinder 362a.

Fixing portions 262d may include a second washer portion 362d', having a washer shape, and a second cylinder portion 362d" having a cylindrical shape and connected to an internal side surface of the second washer portion 362d'. A pair of fixing portions 262d may be disposed on an internal upper surface and an internal lower surface of the first washer portion 306a" of the thermal anchor, respectively.

The external cylinder portion 362b may include a plurality of auxiliary external cylinder portions disposed to be spaced apart from each other. The auxiliary external cylinder portion may be disposed to surround the second cylinder portion 362d" of the fixing portion 262d.

A heat shielding layer 362c may be disposed between the auxiliary external cylinder portion and the auxiliary internal cylinder portion.

Each of the thermal anchors 306a, 306b, and 306c may further include a washer-shaped auxiliary washer portion 306a'" connected to an internal side of the first cylinder portion from a center of the first cylinder portion. The auxiliary washer portion 306a'" may have a slit formed in an azimuthal direction. A refrigerant, evaporated through the slit, may be provided to a condenser 159 through a refrigerant exhaust tube 153.

Figure 15:
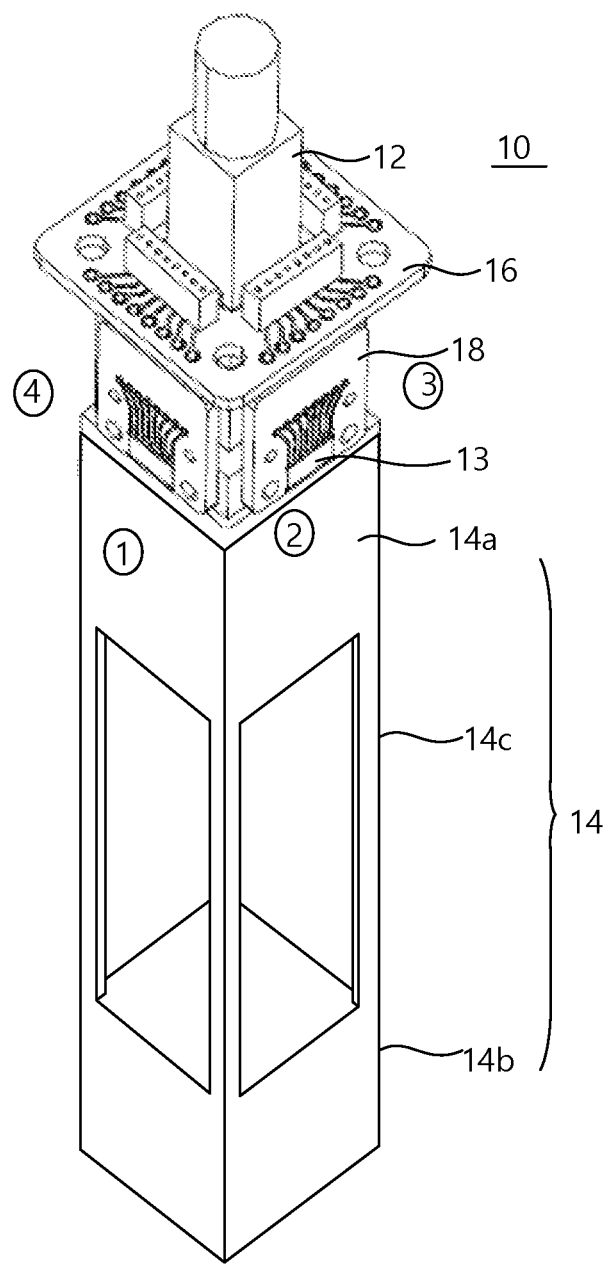
FIG. 15 is a perspective view of a SQUID sensor module according to an example embodiment of the present disclosure.

FIG. 15 is a perspective view of a SQUID sensor module according to an example embodiment of the present disclosure.

Figure 16:
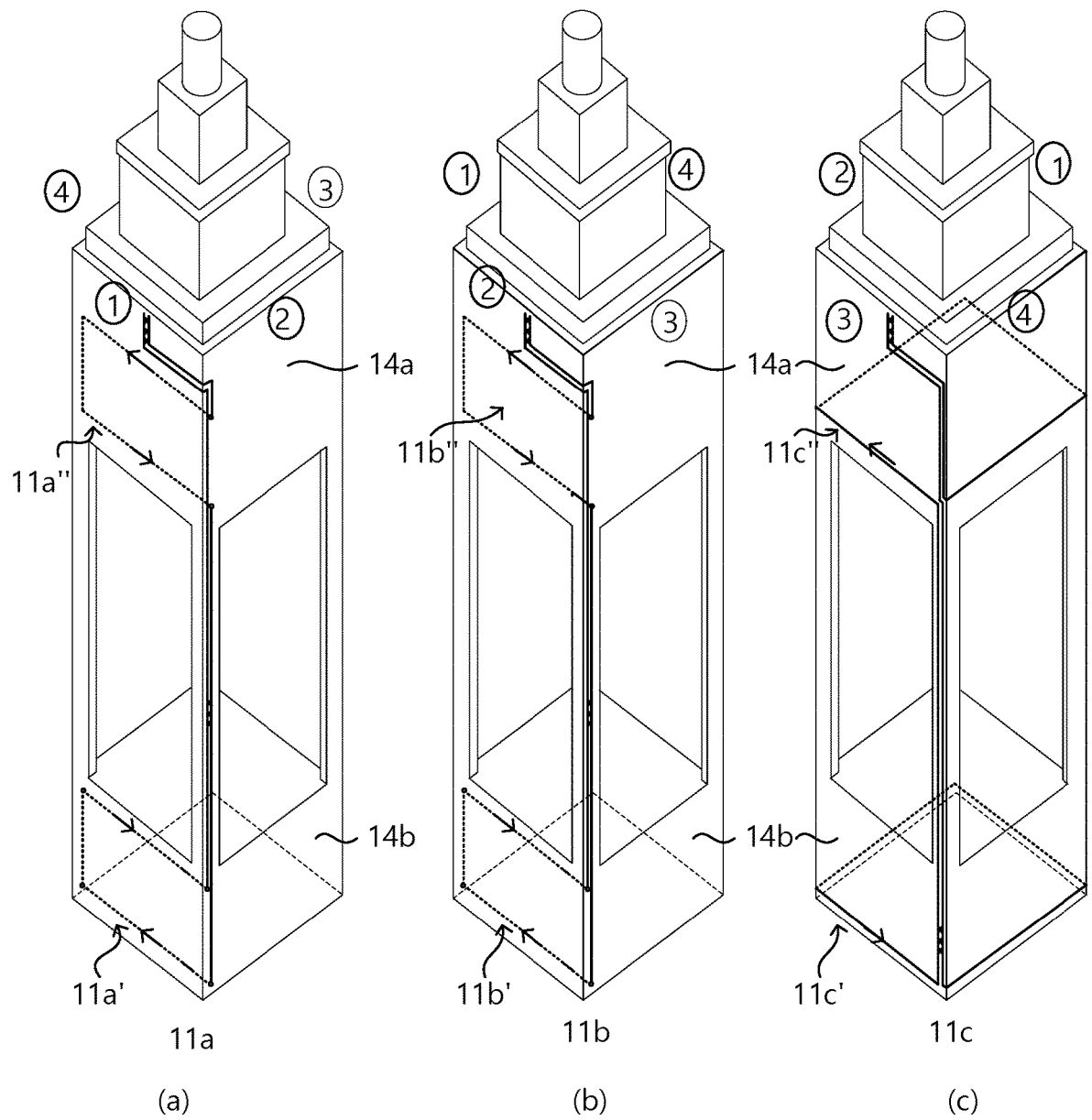
FIG. 16 is a perspective of a pick-up coil of a gradiometer of the SQUID sensor module in FIG. 15.

FIG. 16 is a perspective of a pick-up coil of a gradiometer of the SQUID sensor module in FIG. 15.

Referring to FIGS. 15 and 16, a SQUID sensor module 10 according to an embodiment may include a bobbin 14, on which pick-up coils 11a, 11b, and 11c are mounted, having a cuboidal shape having a rectangular cross section; a fixing block 12 connected to the bobbin 14 and inserted into a hole, formed in a SQUID sensor module mounting plate 120, to be fixed; a SQUID printed circuit board (PCB) 13 mounted on at least one surface, among upper side surfaces of the bobbin 14, and including a superconducting quantum interference device (SQUID) sensor 13; and a signal line connection PCB 16 inserted into the fixing block 12 and transmitting a signal, detected by the SQUID sensor 13, to an external circuit.

The bobbin 14 includes a lower bobbin 14b having a cuboidal shape; an upper bobbin 14a vertically spaced apart from the lower bobbin 14b to be aligned therewith; and a bobbin connecting pillar 14c disposed on each corner to connect the lower bobbin 14b and the upper bobbin 14a to each other. The bobbin 14 may be integrally formed of a non-magnetic material such as G10 epoxy.

Each of the pick-up coils 11a, 11b, and 11c may be a gradiometer. The pick-up coil may include a first gradiometer 11a disposed on a first side surface 1 of the bobbin 14 having first to fourth side surfaces 1, 2, 3, and 4, a second gradiometer 11b disposed on a second side surface 2 adjacent to the first side surface 1 of the bobbin 14, and a third gradiometer 11c disposed on a cross section of the bobbin 14.

In the case of a gradiometer, the gradiometer may include a signal coil 11a' and a reference coil 11a". The signal coil 11a' and the reference coil 11a" may be wound in opposite directions. Accordingly, the gradiometer may measure a differential value of a magnetic signal. As a result, most of uniform external environmental noise may be removed, and a magnetic signal generated by a signal source close to a signal coil may be relatively less canceled to increase a signal-to-noise ratio (SNR).

The signal coil 11a' of the first gradiometer 11a may be disposed on the first side surface 1 of the lower bobbin 14b, and the reference coil 11a" may be disposed on the first side surface 1 of the upper bobbin 14a. The signal coil 11a' may penetrate through the lower bobbin 14b to be adjacent to the first side surface 1.

The signal coil 11b' of the second gradiometer 11b may be disposed on the second side surface 2 of the lower bobbin 14b, and the reference coil 11b" may be disposed on the second side surface 2 of the upper bobbin 14a.

The signal coil 11c' of the third gradiometer 11c may be disposed to surround a lower surface of the lower bobbin 14b, and the reference coil 11c" may be disposed to surround the upper bobbin 14a.

The fixing block 12 may be integrally formed of a non-magnetic material such as G10 epoxy. The fixing block 12 may be inserted into a through-hole formed in the SQUID sensor module mounting plate 120 to be fixed through a nut.

The signal line connection PCB 16 may have a shape of a rectangular plate having a rectangular through-hole in a center thereof, and the signal line connection PCB 16 may be coupled to an external circumferential surface of the fixing block 12. The signal line connection PCB 16 may include a connector. The connector may be connected to an external circuit through a signal line.

The SQUID printed circuit board 18 may be disposed on each side surface of the fixed block 12. The pick-up coils 11a, 11b, and 11c may be electrically connected to the SQUID sensor 13 through a connection line formed of a superconducting material. The connection line may have a niobium (Nb) material.

The SQUID printed circuit board 18 may include a SQUID sensor 18 and a connector disposed on a PCB. The SQUID sensor 18 may be in the form of a semiconductor chip.

When a gradiometer is used, a signal having a high SNR may be obtained in a magnetically shielded room having a lower shielding rate than the magnetometer. However, since a length of the gradiometer is significantly greater than a length of a magnetometer, a volume occupied by the gradiometer may be increased to increase an area receiving radiant heat introduced at room temperature, which may cause an evaporation rate of a low-temperature refrigerant to be significantly increased. A bobbin of the gradiometer may include a lower bobbin 14b and an upper bobbin 14a, spaced apart from each other to significantly decrease capacity, and a bobbin connection pillar 14c disposed on each corner.

As described above, a magnetic field measuring apparatus according to an example embodiment may easily replace a SQUID sensor module.

A magnetic field measuring apparatus according to an example embodiment may efficiently block radiant heat using a neck portion having a double-wall structure.

A magnetic field measuring apparatus according to an example embodiment may block permeation of a refrigerant into a vacuum layer using a neck portion having a double-wall structure.

A magnetic field measuring apparatus according to an example embodiment may improve sensor cooling and may efficiently decrease an evaporation rate of liquid helium by bring a thermal anchor, mounted in a neck portion having a double-wall structure, into direct contact with an evaporated refrigerant.

A magnetic field measuring apparatus according to an example embodiment may reduce vibration by mounting a pick-up coil on a lower surface of a vacuum layer of an internal container.

A magnetic field measuring apparatus according to an example embodiment may improve operation reliability by mounting a pick-up coil and a SQUID on a lower surface of a vacuum layer of an internal container.

A magnetic field measuring apparatus according to an example embodiment may increase efficiency of a condenser or a cooler by delivering a cool helium gas, evaporated in a Dewar, to a condenser using a coaxial dual tube structure connecting the condenser and the Dewar to each other.

A magnetic field measuring apparatus according to an example embodiment may increase a signal-to-noise ratio (SNR) by employing a coil-in-vacuum (CIV) structure to reduce a distance between a SQUID sensor and a current source.

A magnetic field measuring apparatus according to an example embodiment may increase measurement accuracy of a signal source using a triaxial gradiometer.

A magnetic field measuring apparatus according to an example embodiment may include a main thermal anchor for cooling a SQUID sensor on a lower surface of an internal container storing a refrigerant. The main thermal anchor may include of a plurality of components to increases a thermal contact area while inhibiting damage to the internal container caused by thermal expansion, and thus, may efficiently cool a SQUID sensor through a litz wire.

Although the present disclosure and its advantages have been described in detail, it should be understood that various changes, substitutions and alterations can be made herein without departing from the spirit and scope of the disclosure as defined by the following claims.

What is claimed is:

1. A magnetic field measuring apparatus comprising:
an external container;
an internal container storing a liquid refrigerant, disposed inside the external container, and including a neck portion having a first diameter and a body portion having a second diameter greater than the first diameter, wherein a space between the internal container and the external container is maintained in a vacuum state;
a SQUID sensor module mounting plate disposed below the internal container;
a plurality of SQUID sensor modules mounted below the SQUID sensor module mounting plate;
a 4K heat shielding portion formed of a conductive mesh disposed to surround the SQUID sensor module mounting plate and the plurality of SQUID sensor modules;
a main thermal anchor cooled by the refrigerant and disposed on a lower surface of the internal container;
a ring-shaped auxiliary thermal anchor coupled to a side surface of the SQUID sensor module mounting plate with the 4K heat shielding portion interposed therebetween and fixing the 4K heat shielding portion; and
a litz wire connecting and cooling the main thermal anchor and the auxiliary thermal anchor.

2. The magnetic field measuring apparatus as set forth in claim 1, further comprising:
a sensor guide rod mounted on a lower surface of the internal container, extending through the SQUID sensor module mounting plate, and guiding a vertical motion of the SQUID sensor module mounting plate; and
a sensor fixing rod mounted on the lower surface of the internal container and fixed to the SQUID sensor module mounting plate.

3. The magnetic field measuring apparatus as set forth in claim 1, wherein the SQUID sensor modules penetrate through the SQUID sensor module mounting plate and are arranged in a first direction and a second direction,
each of the SQUID sensor modules vertically extends, and
wherein the magnetic field measuring apparatus further comprises a plurality of heat transfer rods extending parallel to the SQUID sensor modules,
the heat transfer rods penetrate through the SQUID sensor module mounting plate, and
both ends of the heat transfer rods are each connected to the 4K heat shielding portion.

4. The magnetic field measuring apparatus as set forth in claim 1, further comprising:
a refrigerant exhaust tube disposed at a baffle insert and exhausting an evaporated refrigerant;
a refrigerant injection tube disposed at the baffle insert and injecting a refrigerant; and
a condenser connected to the refrigerant exhaust tube and the refrigerant injection tube and condensing an evaporated refrigerant exhausted through the refrigerant injection tube,
wherein the refrigerant exhaust tube and the refrigerant injection tube have a coaxial structure, and
each of the refrigerant exhaust tube and the refrigerant injection tube is a dual tube including an internal tube and an external tube.

5. The magnetic field measuring apparatus as set forth in claim 1, wherein the SQUID sensor module mounting plate includes a curved portion, and
the curved portion is disposed to surround left ventricle of heart.

6. The magnetic field measuring apparatus as set forth in claim 1, wherein the SQUID sensor module mounting plate is provided with ring-shaped ring dent portion on a lower surface of a side surface of the SQUID sensor module mounting plate,
the SQUID sensor module mounting plate includes at least one connection portion penetrating through the SQUID sensor module mounting plate in the ring dent portion, and
the auxiliary thermal anchor includes at least one projection coupled to the ring dent portion and protruding to be insertable into the connection portion.

7. The magnetic field measuring apparatus as set forth in claim 6, wherein the 4K heat shielding portion comprises:
- an upper 4K heat shielding portion disposed on an upper surface of the SQUID sensor module mounting plate; and
- a lower 4K heat shielding portion disposed surround the plurality of SQUID sensor modules, and
- wherein the auxiliary thermal anchor is coupled to a side surface of the SQUID sensor module mounting plate with the lower 4K heat shielding portion interposed therebetween.

8. The magnetic field measuring apparatus as set forth in claim 1, wherein the SQUID sensor modules are arranged in a matrix in a first direction and a second direction, perpendicular to the first direction, and
- wherein the SQUID sensor module mounting plate further includes a trench extending in the first direction on the SQUID sensor mounting plate between SQUID sensor modules, arranged in the first direction, and SQUID sensor modules spaced apart from each other in the second direction to be arranged in the first direction.

9. The magnetic field measuring apparatus as set forth in claim 8, further comprising:
- signal line connection holes connected to the trench, arranged at regular intervals in the first direction, and penetrating through the SQUID sensor module mounting plate.

10. The magnetic field measuring apparatus as set forth in claim 9, wherein the SQUID sensor module mounting plate is provided with a ring-shaped ring dent portion on a lower surface of a side surface of the SQUID sensor module mounting plate,
- the SQUID sensor module mounting plate includes at least one connection portion penetrating through the SQUID sensor module mounting plate in the ring dent portion,
- the ring-shaped auxiliary thermal anchor includes at least one projection coupled to the ring dent portion and protruding to be insertable into the connection portion, and
- the magnetic field measuring apparatus further comprises a trench disposed on an outermost side in the first direction, connected to the connection portion.

11. The magnetic field measuring apparatus as set forth in claim 1, wherein internal container comprises:
- a neck portion into which a baffle insert is inserted; and
- a body portion having an increased diameter as compared with the neck portion, and
- wherein the neck portion itself has a double-wall structure including an internal cylinder and an external cylinder surrounding the internal cylinder.

12. The magnetic field measuring apparatus as set forth in claim 11, wherein the internal cylinder further includes a plurality of ring projections protruding outwardly of a cylinder,
- thermal anchors are coupled to the ring projections, respectively,
- the ring projections are disposed to be spaced apart from each other, and
- the external cylinder is separated into external cylinders with the ring projection interposed therebetween.

13. The magnetic field measuring apparatus as set forth in claim 12, wherein the neck portion further includes a heat shielding layer disposed between the internal cylinder and the external cylinder.

14. The magnetic field measuring apparatus as set forth in claim 12, wherein an external circumferential surface of the ring projection and an internal circumferential surface of the thermal anchors are screw-coupled to each other.

15. The magnetic field measuring apparatus as set forth in claim 12, wherein the thermal anchors include first to third thermal anchors having a washer shape and vertically spaced apart from each other to be sequentially arranged on an external side of the neck portion,
- the first thermal anchor is connected to a 120K heat shielding layer,
- the second thermal anchor is connected to an 80K heat shielding layer,
- the third thermal anchor is connected to a 40K heat shielding layer, and
- the 40K heat shielding layer is disposed to the 4K heat shielding portion.

16. The magnetic field measuring apparatus as set forth in claim 15, wherein each of the first to third thermal anchors is provided with a plurality of slits.

17. The magnetic field measuring apparatus as set forth in claim 1, wherein the main thermal anchor comprises:
- a first heat transfer unit formed of oxygen-free copper and including a first disc, and a first lower projection protruding from a central axis of the first disc to a lower surface of the first disc;
- a second heat transfer unit formed of oxygen-free copper and including a second disc, a second upper projection protruding from a central axis of the second disc to an upper surface of the second disc, and a second lower projection protruding from the central axis of the second disc to a lower surface of the second disc;
- a third heat transfer unit formed of oxygen-free copper and including a third disc, a third upper projection protruding from a central axis of the third disc to an upper surface of the third disc, and a third lower projection protruding from the central axis of the third disc to a lower surface of the third disc;
- a fourth heat transfer unit formed of oxygen-free copper and including a fourth disc, a fourth upper projection protruding from a central axis of the fourth disc to an upper surface of the fourth disc, and a fourth lower projection protruding from the central axis of the fourth disc to a lower surface of the fourth disc;
- a first thermal expansion control unit formed of an insulating material and inserted between the first disc of the first heat transfer unit and the second disc of the second heat transfer unit; and
- a second thermal expansion control unit formed of an insulating material and inserted between the third disc of the third heat transfer unit and the fourth disc of the fourth heat transfer unit, and
- wherein the second upper projection of the second transfer unit is provided with a groove for coupling to the first lower projection of the first heat transfer unit,
- the second lower projection of the second heat transfer unit has a groove for coupling to the third upper projection of the third heat transfer unit, and
- the third lower projection of the third heat transfer unit has a groove for coupling to the fourth upper projection of the fourth heat transfer unit.

18. The magnetic field measuring apparatus as set forth in claim 17, wherein the first thermal expansion control unit comprising:
- a first insulating body portion having the same diameter as a first diameter of the first disc;
- a second insulating body portion embedded in a lower surface of the internal body and having a second diameter greater than the first diameter; and a third insulating body portion having a third diameter smaller than the second diameter, and
wherein the third insulating body portion is disposed to surround an external circumferential surface of the second disc.

19. The magnetic field measuring apparatus as set forth in claim 1, wherein the internal container comprises:
a neck portion into which a baffle insert is inserted; and
a body portion having an increased diameter as compared with the neck portion, and
wherein the neck portion includes an internal cylinder portion and an external cylinder portion disposed to surround the internal cylinder portion,
the internal cylinder portion are separated into auxiliary internal cylinders disposed to be vertically spaced apart from each other, and
thermal anchors between the separated auxiliary internal cylinders.

20. The magnetic field measuring apparatus as set forth in claim 19, wherein each of the thermal anchors comprises:
a first cylinder portion having a cylindrical shape; and
a first washer portion having a washer shape and connected to an external side of the first cylinder portion from a center of the first cylinder portion, and
wherein an external side surface of the first cylinder portion is screw-coupled to an internal side surface of a corresponding auxiliary internal cylinder.

21. The magnetic field measuring apparatus as set forth in claim 20, further comprising:
fixing portions including a second washer portion, having a washer shape, and a second cylinder portion having a cylindrical shape and connected to an internal side surface of the second washer portion,
wherein a pair of fixing portions are disposed on an internal upper surface and an internal lower surface of the first washer portion of the thermal anchors, respectively.

22. The magnetic field measuring apparatus as set forth in claim 21, wherein the external cylinder portion includes a plurality of auxiliary external cylinder portions disposed to be spaced apart from each other,
the auxiliary external cylinder portion is disposed to surround the second cylinder portion of the fixing portion, and
a heat shielding layer is disposed between the auxiliary external cylinder portion and the auxiliary internal cylinder portion.

23. The magnetic field measuring apparatus as set forth in claim 22, wherein each of the thermal anchors further includes an auxiliary washer portion having a washer shape and connected to an internal side of the first cylinder portion from a center of the first cylinder portion, and the auxiliary washer portion has a slit formed in an azimuthal direction.

24. The magnetic field measuring apparatus as set forth in claim 1, wherein each of the SQUID sensor modules comprises:
a cuboidal bobbin, on which a pick-up coil is mounted, having a rectangular cross section;
a fixing block connected to the bobbin and inserted in a hole, formed in the SQUID sensor module mounting plate, to be fixed;
a SQUID printed circuit board (PCB) mounted on at least one surface, among upper side surfaces of the bobbin, and including a superconducting quantum interference device (SQUID) sensor; and
a signal line connection PCB inserted into the fixing block and transferring a signal, detected by the SQUID sensor, to an external circuit.

25. The magnetic field measuring apparatus as set forth in claim 24, wherein the pick-up coil is a gradiometer, and
wherein the pick-up coil comprises:
a first gradiometer disposed on a first side surface, having a rectangular cross section, of the bobbin;
a second gradiometer disposed on a second side surface adjacent to the first side surface of the bobbin; and
a third gradiometer disposed on a lower surface of the bobbin.

26. A magnetic field measuring apparatus comprising:
an external container; and
an internal container storing a liquid refrigerant and inserted into the external container,
wherein the internal container comprises:
a neck portion into which a baffle insert is inserted; and
a body portion having an increased diameter as compared with the neck portion, and
wherein the neck portion includes an internal cylinder portion and an external cylinder portion disposed to surround the internal cylinder portion,
the internal cylinder portion is separated into auxiliary internal cylinders disposed to be vertically spaced apart from each other, and
thermal anchors are each inserted between the separated auxiliary internal cylinders,
wherein each of the thermal anchors comprises:
a first cylinder portion having a cylindrical shape; and
a first washer portion having a washer shape and connected to an external side of the first cylinder portion from a center of the first cylinder portion,
wherein an external side surface of the first cylinder portion is screw-coupled to an internal side surface of a corresponding auxiliary internal cylinder.

* * * * *